US008524479B2

(12) United States Patent
Nett

(10) Patent No.: US 8,524,479 B2
(45) Date of Patent: Sep. 3, 2013

(54) URA5 GENE AND METHODS FOR STABLE GENETIC INTEGRATION IN YEAST

(75) Inventor: Juergen H. Nett, Grantham, NH (US)

(73) Assignee: GlycoFi, Inc., Lebanon, NH (US)

( * ) Notice: Subject to any disclaimer, the term of this patent is extended or adjusted under 35 U.S.C. 154(b) by 0 days.

(21) Appl. No.: 13/268,061

(22) Filed: Oct. 7, 2011

(65) Prior Publication Data

US 2012/0116058 A1 May 10, 2012

Related U.S. Application Data

(62) Division of application No. 12/321,512, filed on Jan. 22, 2009, now Pat. No. 8,062,879, which is a division of application No. 10/454,125, filed on Jun. 3, 2003, now Pat. No. 7,514,253.

(60) Provisional application No. 60/471,435, filed on May 16, 2003.

(51) Int. Cl.
*C12N 9/12* (2006.01)

(52) U.S. Cl.
USPC .......................... 435/194; 435/183; 530/350

(58) Field of Classification Search
None
See application file for complete search history.

(56) References Cited

U.S. PATENT DOCUMENTS 6,051,419 A    4/2000 Gleeson et al.
7,001,751 B1   2/2006 Pfaller

OTHER PUBLICATIONS

Qiagen Product Guide 2002.*
Ngo et al. In the Protein Folding Problem and Tertiary Structure Prediction, 1994, Merz et al. (ed.), Birkhauser, Boston, MA, pp. 433 and 492-495.*
Abeijon, "Molecular cloning of the Golgi apparatus . . . ", Proc. Natl. Acad. Sci. USA, pp. 5963-5968, vol. 93 (1996).
Alani, "A method or gene disruption . . . ", Genetics, vol. 116, pp. 541-545, (1987).
Altschul, "Basic local alignment search tool", J. Mol. Biol.,vol. 215, pp. 403-410, (1990).
Altschul, "Gapped BLAST and PSI-BLAST: . . . ", Nucleic Acids Res., vol. 25, pp. 3389-3402, (1997).
Bai, "The URA5 gene encoding orotate-phosphoribosyl . . . ", Yeast, vol. 15, pp. 1393-1398, (1999).
Boehm, "Disruption of the KEX1 gene in *Pichia pastoris* . . . ", Yeast, vol. 15, pp. 563-572, (1999).
Boeke, "5-Fluoroorotic acid as a selective agent . . . ", Meth. Enzymo., vol. 154, pp. 164-175, (1987).
Boeke, "A positive selection for mutants lacking . . . ", Mol. Gen. Genet., vol. 197, pp. 345-346, (1984).
Caldwell, "Randomization of genes by PCR mutagenesis", PCR Methods Applic., vol. 2, pp. 28-33, (1992).
Choi, "Use of combinatorial genetic libraries . . . ", Proc. Natl. Acad. Sci., vol. 100, pp. 5022-5027, (2003).
Chung, "Enzymatic kinetic analyses that employ . . . ", J. Chromatography , vol. 371, pp. 71-81, (1986).
Cregg, "*Pichia pastoris* as a host system . . . ", Mol. Cell Biol., vol. 5, pp. 3376-3385 (1985).
Datasbase Geneseq (online) XP002485502, GSP:ABP74016 (2003).
Dunn, "Synthesis of monohydroxylated inositolphorylceramide . . . ", Yeast, vol. 14, pp. 311-321, (1998).
Fonzi, "Isogenic strain construction and gene mapping . . . ", Genetics, vol. 134, pp. 717-728, (1993).
Gish, "Identification of protein coding regions ,..", Nature Genet., vol. 3, pp. 266-272, (1993).
Gould, Development of the yeast *Pichia pastoris* as a model . . . n, Yeast, vol. 8, pp. 613-628 (1992).
Grubmeyer, "Active site lysines in orotate . . . ", J. Biol. Chem. , vol. 268, pp. 20299-20304, (1993).
Guldener, "A neW efficient gene disruption cassette . . . ", Nucleic Acids Res., vol. 24, pp. 2519-2524 (1996).
Haak, "Hydroxylation of *Saccharomyces cerevisiae* ceramides . . . ", J. Biol. Chem., vol. 272, pp. 29704-29710 (1997).
Hann, "SEC65 gene product is a subunit of the yeast signal . . . ", Nature, vol. 356, pp. 532-533 (1992).
Higgins, "*Pichia* protocols", Meth. Mol. Biol. , vol. 103, pp. 1-15 (1998).
Higgins, "*Pichia* protocols", Method Mol. Biol., vol. 103, pp. 41-53 (1993).
Jund, "Regulation of ortotydylic acid pyrophosphorylase . . . ", J. Bacteriol. , vol. 109, pp. 196-202, (1989).
Kalnins, "Sequence of the lacZ gene of *E. coli*", EMBO J., vol. 2, pp. 593-597 (1983).
Kimura, "Cloning of the blasticidin S deaminase gene (BSD) . . . ", Mol. Gen. Genet., vol. 242, pp. 121-129 (1994).
Leung, "A method for random mutagenesis of a defined DNA",. , Technique, pp. 11-15, vol. 1 (1989).
Lin Cereghino, "New selectable marker/auxotrophic host strain combinations ..", Gene, pp. vol. 3, 159-169, (2001).
Lu, "Cloning and disruption of the beta•isopropylmalate . . . ", Appl. Microbiol. Biotechnol., vol. 49, pp. 141-146, (1998).
Madden, "Applications of network BLAST server", Meth. Enzymol., vol. 266, pp. 131-141, (1996).
Montigny, "Structure and expression of the URA5 gene . . . ", Mol. Gen. Genet., vol. 215, pp. 455-462 (1989).
Montigny, "Cloning and sequencing of URA10, a second gene ..", Curro Genet. , vol. 17, pp. 105-111 (1990).
Orr-Weaver, "Yeast recombination: The association between doublestrand . . . ", Proc. Natl. Acad. Sci. USA, vol. 78, pp. 4417-4421 (1983).
Nett, "Cloning and disruption of the PpURA5 gene . . . ", Yeast, vol. 20, pp. 1279-1290 (2003).
Ngo, et al., In the Protein Folding Problem and Tertiary Structure Prediction, Merz et al., (ed.), Birkhauser, Boston, MA, pp. 433 and 493-495 (1994).
Pearson, "Rapid and sensitive sequence comparison . . . ", Methods Enzymol., vol. 183, pp. 63-98, (1990).
Pearson, "Using FASTA program to search protein and DNA . . . ", Methods Mol. Biol. , vol. 24, pp. 307-331, and pp. 365-389, vol. 25 (1994).

(Continued)

*Primary Examiner* — Richard Hutson
(74) *Attorney, Agent, or Firm* — Patricia L. Chisholm; Immac J. Thampoe

(57) ABSTRACT

A novel gene encoding *P. pastoris* orotate-phosphoribosyl transferase (URA5) is disclosed. Methods for producing and selecting yeast strains capable of stable genetic integration of heterologous sequences into the host genome are also provided.

3 Claims, 6 Drawing Sheets

(56) References Cited

OTHER PUBLICATIONS

Posnett, "A novel method for producing anti-peptide . . . ", J. Biol. Chem., vol. 263, pp. 1719-1725 (1998).
Regnacq, "Deletion analysis of yeast Sec65p . . . ", Mol. Microbial., vol. 29, pp. 753-762 (1998).
Reidhaar-Olson, "Combinatorial cassette mutagenesis as a probe . . . ", Science, vol. 241, pp. 53-57 (1988).
Rose, "Consensus-degenerate hybrid ollgonucleotide primers . . . ", Nucleic Acids Res., vol. 26, pp. 1628-1635 (1998).
Rossanese, "Golgl structure correlates with transitional endoplasmic . . . ", J. Cell Biol., vol. 145, pp. 69-81 (1999).
Sakai, "Peroxisome degradation by microautophagy in *Pichia pastoris*: . . . ", J. Cell Biol., vol. 141, pp. 625-636 (1998).
Sambrook, Molecular Cloning: A Laboratory Manual, 2nd ed., Cold Spring Harbor Laboratory Press, Cold Spring Harbor, NY, pp. 9.50-9.51 (1989).
Sanchez, "Gene order in a 10275 bp fragment of *Yarrawia lipolytica* . . . ", Yeast, vol. 18, pp. 807-813 (2001).
Sanchez, M., et. al., "Cloning and Sequencing of the URA5 Gene from the Yeast *Yarrawia lipolytica*", Yeast, vol. 11, pp. 425-433 (1995).
Scherer, "Replacement of chromosome segmens with altered DNA . . . ", Proc. Natl. Acad. Sci. USA (1979).
Shostak, "Direct spectrophotometric assays for orotate . . . ", Anal. Biochem., vol. 191, pp. 365-369 (1990).
Soderholm, "Vector for pop-in/pop-out gene replacement . . . ", BioTechniques, vol. 31, pp. 306-312 (2001).
Stirling, "The *S. cerevisiae* SEC65 gene encodes a component . . . ", Nature, vol. 356, pp. 534-537 (1992).
Tam, "Synthetic peptide vaccine design: . . . ", Proc. Natl. Acad. Sci. USA, vol. 85, pp. 5409-5413 (1988).
Tuttle, "Divergent modes of autophagy in the methylotrophic yeast . . . ", J. Cell Sci., vol. 108, pp. 25-35 (1995).
Wilson, "A recycable *Candida albicans* URA3 cassette for PCR . . . ", Yeast, vol. 16, pp. 65-70 (2000).
Yanisch-Perron, "Improved M13 phage cloning vectors and host strains: . . . ", Gene, vol. 33, pp. 103-119 (1985).
Zhang, "PowerBLAST: A new network BLAST application for interactive..", Genome Res., vol. 7, pp. 649-656 (1997).

* cited by examiner

```
       1  GATCATGGACTAAGGAGTTTTATTTGGACCAAGTTCATCGTCCTAGACATTACGGAAAGG
SCS7 ──────► S  W  T  K  E  F  Y  L  D  Q  V  H  R  P  R  H  Y  G  K
      61  GTTCTGCTCCTCTTTTTGGAAACTTTTTGGAACCTCTGAGTATGACAGCTTGGTGGATTG
           G  S  A  P  L  F  G  N  F  L  E  P  L  S  M  T  A  W  W  I
     121  TACCCATGGTATGGCTTCCTGTGAATTTCTATTTTTTCTACATTGGATTCACCAATCAAA
           V  P  M  V  W  L  P  V  N  F  Y  F  F  Y  I  G  F  T  N  Q
     181  ACAAATTAGTCGCCATGGCTTTTTGGCTTTTGGGTCTATTTGTTTGGACCTTCTTGGAAT
           N  K  L  V  A  M  A  F  W  L  L  G  L  F  V  W  T  F  L  E
     241  ATGCTTTGCATAGATTTTTGTTCCACTTGGACTACTATCTTCCAGAGAATCAAATTGCAT
           Y  A  L  H  R  F  L  H  D  Y  Y  L  P  E  N  Q  I  A
     301  TTACCATTCATTTCTTATTGCATGGGATACACCACTATTTACCAATGGATAAATACAGAT
           F  T  I  H  F  L  L  H  G  I  H  H  Y  L  P  M  D  K  Y  R
     361  TGGTGATGCCACCTACACTTTTCATTGTACTTTGCTACCCAATCAAGACGCTCGTCTTTT
           L  V  M  P  P  T  L  F  I  V  L  C  Y  P  I  K  T  L  V  F
     421  CTGTTCTACCATATTACATGGCTTGTTCTGGATTTGCAGGTGGATTCCTGGGCTATATCA
           S  V  L  P  Y  Y  M  A  C  S  G  F  A  G  G  F  L  G  Y  I
     481  TGTATGATGTCACTCATTACGTTCTGCATCACTCCAAGCTGCCTCGTTATTTCCAAGAGT
           M  Y  D  V  T  H  Y  V  L  H  H  S  K  L  P  R  Y  F  Q  E
     541  TGAAGAAATATCATTTGGAACATCACTACAAGAATTACGAGTTAGGCTTTGGTGTCACTT
           L  K  K  Y  H  L  E  H  H  Y  K  N  Y  E  L  G  F  G  V  T
     601  CCAAATTCTGGGACAAAGTCTTTGGGACTTATCTGGGTCCAGACGATGTGTATCAAAAGA
           S  K  F  W  D  K  V  F  G  T  Y  L  G  P  D  D  V  Y  Q  K
     661  CAAATTAGAGTATTTATAAAGTTATGTAAGCAAATAGGGGCTAATAGGGAAAGAAAAATT
           T  N  *
     721  TTGGTTCTTTATCAGAGCTGGCTCGCGCGCAGTGTTTTCGTGCTCCTTTGTAATAGTCA
     781  TTTTTGACTACTGTTCAGATTGAAATCACATTGAAGATGTCACTCGAGGGGTACCAAAAA
                                          URA5 ──────► M  S  L  E  G  Y  Q  K
     841  AGGTTTTTGGATGCTGCAGTGGCTTGCGAGGCCTTGAAGTTTGGAACTTTCACCTTGAAA
           R  F  L  D  A  A  V  A  S  Q  A  L  K  F  G  T  F  T  L  K
     901  AGTGGAAGACAGTCTCCATACTTCTTTAACATGGGTCTTTTCAACAAAGCTCCATTAGTG
           S  G  R  Q  S  P  Y  F  F  N  M  G  L  F  N  K  A  P  L  V
     961  AGTCAGCTGGCTGAATCTTATGCTCAGGCCATCATTAACAGCAACCTGGATAGACGTT
           S  Q  L  A  E  S  Y  A  Q  A  I  I  N  S  N  L  E  I  D  V
    1021  GTATTTGGACCAGCTTATAAAGGTATTCCTTTGGCTGCTATTACCGTGTTGAAGTTGTAC
           V  F  G  P  A  Y  K  G  I  P  L  A  A  I  T  V  L  K  L  Y
    1081  GAGCTCGGCGGCAAAAAATACGAAAATGTCGGATATGCGTTCAATAGAAAAGAAAAGAAA
           E  L  G  G  K  K  Y  E  N  V  G  Y  A  F  N  R  K  E  K  K
    1141  GACCACGGAGAAGGTGGAAGCATCGTTGGAGAAAGTCTAAAGAATAAAAGAGTACTGATT
           D  H  G  E  G  G  S  I  V  G  E  S  L  K  N  K  R  V  L  I
    1201  ATCGATGATGTGATGACTGCAGGTACTGCTATCAACGAAGCATTTGCTATAATTGGAGCT
           I  D  D  V  M  T  A  G  T  A  I  N  E  A  F  A  I  I  G  A
    1261  GAAGGTGGGAGAGTTGAAGGTTGTATTATTGCCCTAGATAGAATGGAGACTACAGGAGAT
           E  G  G  R  V  E  G  C  I  I  A  L  D  R  M  E  T  T  G  D
    1321  GACTCAAATACCAGTGCTACCCAGGCTGTTAGTCAGAGATATGGTACCCCTGTCTTGAGT
           D  S  N  T  S  A  T  Q  A  V  S  Q  R  Y  G  T  P  V  L  S
    1381  ATAGTGACATTGGACCATATTGTGGCCCATTTGGGCGAAACTTTCACAGCAGACGAGAAA
           I  V  T  L  D  H  I  V  A  H  L  G  E  T  F  T  A  D  E  K
    1441  TCTCAAATGGAAACGTATAGAAAAAAGTATTTGCCCAAATAAGTATGAATCTGCTTCGAA
           S  Q  M  E  T  Y  R  K  K  Y  L  P  K  *
    1501  TGAATGAATTAATCCAATTATCTTCTCACCATTATTTTCTTCTGTTTCGGAGCTTTGGGC
                           *  R  R  V  M  I  K  K  Q  K  P  A  K  P
    1561  ACGGCGGCGGGTGGTGCGGGCTCAGGTTCCCTTTCATAAACAGATTTAGTACTTGGATGC
           V  A  A  P  P  A  P  E  P  E  R  E  Y  V  S  K  T  S  P  H
    1621  TTAATAGTGAATGGCGAATGCAAAGGAACAATTTCGTTCATCTTTAACCCTTTCACTCGG
           K  I  T  F  P  S  H  L  P  V  I  E  N  M  K  L  G  K  V  R
    1681  GGTACACGTTCTGGAATGTACCCGCCCTGTTGCAACTCAGGTGGACCGGGCAATTCTTGA
           P  V  R  E  P  I  Y  G  G  Q  Q  L  E  P  P  G  P  L  E  Q
    1741  ACTTTCTGTAACGTTGTTGGATGTTCAACCAGAAATTGTCCTACCAACTGTATTAGTTTC
           V  K  F  Q  G  V  L  Q  I  L  K
    1801  CTTTTGGTCTTATATTGTTCATCGAGATACTTCCCACTCTCCTTGATAGCCACTCTCACT
           R  K  T  K  Y  Q  E  D  L  Y  K  G  S  E  K  I  A  V  R  V
    1861  CTTCCTGGATTACCAAAATCTTGAGGATGAGTCTTTTCAGGCTCCAGGATGCAAGGTATA
           R  G  P  N  G  F  D  Q  P  H  T  K  E  P  E  L  I  C  P  I
    1921  TCCAAGTACCTGCAAGCATCTAATATT
           D  L  Y  R  C  A  D  L  I ──────SEC65
```

FIG. 1

```
              Ura5-1 ->
P. pastoris   LKSGRQSPYFFNMGLFNKAPLVSQLAESYAQAIINS----NLEIDVVFGPAYKGIPLA
S. c. Ura5    LKSGRESPYFFNLGLFNTGKLLSNLATAYAIAIIQS----DLKFDVIFGPAYKGIPLA
S. c. Ura10   LNSGRQSPYFFNLSLFNSGKLLANLATAYATAIIQS----ELKFDVIFGPAYKGIPLA
K. lactis     LKSGRVSPYFFNLGLFNTGKLLSNLATAYAIAIIQS----ELKFDVIFGPAYKGIPLA
Y. lipolytica LKSGRTSPYFFNLGLFNTGVALSTVGASFAQVIINS----GVEFDVIFGPAYKGIPLA
S. pombe      LKSGRKSPYFFNSGNFTHGADLCALAEAYAETIIAM----NVDFDVIFGPAYKGISLA
T. reesei     LKSKRISPYFFNAGEFHTARLARRIASAFAKTIIEAQEKAGLEFDIVFGPAYKGIPLC
E. coli       LKSGRKSPYFFNAGLFNTGRDLALLGRFYAEALVDS----GIEFDLLFGPAYKGIPLA
P. aeruginosa LKSGRTSPYFFNAGLFDSGLALARLGRFYAEAVIDS----GIDFDVLFGPAYKGIPLA
H. influenzae LKSGRKSPYFFNAGLFNTGADLARLGEFYAAAIQAS----AVDFDVVFGPAYKGIPIG
              27                                                        80

Sec65-1 ->
S. cerevisiae YPCYFDINRSHKEGRRVPKELAVENPLAKTMADAVRELGILCIFEGEKCHPQDFGNPGR
K. lactis     YPCYFDTRRTHAQGRRAPKDLCVENPLAKTIADAARSLGIPSIFEGSKTHPQDFGNPGR
C. albicans   YPCYFDINRSHKQGRRVSIDRAVENPLATTISDACRRLGLPVFLELDKTHPQDFGNPGR
Y. lipolytica YPVYFDKNKTVGEGRRVPLELAVENPLGQTIAEEACKMLTLPSIYEAHKTHPKDWANPGR
N. crassa     YPCYFDATRSRAEGRRVSKELAVPNPLATEIVNACAQLRLSVVLEAGKLHPKDWANPGR
S. pombe      YPIYFDKSRPR-RFRCVPKDKAILNPLAKNIADVVRDLGYKCKLEPLKTHPADWVNPGR
              102                                                      160
```

FIG. 2

DEGENERATE OLIGONUCLEOTIDES USEFUL FOR CLONING OF *P. pastoris* URA5

URA5-1    TTGAAGTCTGGTAGAGAATCTCCATAYTTYTTYAA
URA5-2    TTTGATGTTATTTTTGGTCCAGCNTAYAARGGNAT
URA5-3    AGCCAATGGAATACCCTTGTAAGCNGGNCCRAA
URA5-4    AGAAAGGAAGCTAAGGATCATGGNGARGGNGG
URA5-5    ACCACCTTCACCATGATCCTTNGCYTCYTT
URA5-6    AGCAGTACCAGCAGTCATNACRTCRTC

SEQUENCE LISTING

```
<160> NUMBER OF SEQ ID NOS: 47

<210> SEQ ID NO 1
<211> LENGTH: 1947
<212> TYPE: DNA
<213> ORGANISM: Pichia pastoris

<400> SEQUENCE: 1
gatcatggac taaggagttt tatttggacc aagttcatcg tcctagacat tacggaaagg      60
gttctgctcc tcttttttgga aactttttgg aacctctgag tatgacagct tggtggattg     120
tacccatggt atggcttcct gtgaatttct attttttcta cattggattc accaatcaaa     180
acaaattagt cgccatggct ttttggcttt tgggtctatt tgtttggacc ttcttggaat     240
atgctttgca tagattttg ttccacttgg actactatct tccagagaat caaattgcat      300
ttaccattca tttcttattg catgggatac accactattt accaatggat aaatacagat     360
tggtgatgcc acctacactt ttcattgtac tttgctaccc aatcaagacg ctcgtctttt     420
ctgttctacc atattacatg gcttgttctg gatttgcagg tggattcctg ggctatatca     480
tgtatgatgt cactccattac gttctgcatc actccaagct gcctcgttat tccaagagt     540 tgaagaaata tcatttggaa catcactaca agaattacga gttaggcttt ggtgtcactt     600
```

-continued

```
ccaaattctg ggacaaagtc tttgggactt atctgggtcc agacgatgtg tatcaaaaga      660
caaattagag tatttataaa gttatgtaag caaatagggg ctaatagggga aagaaaaatt     720 ttggttcttt atcagagctg gctcgcgcgc agtgttttc gtgctccttt gtaatagtca      780
tttttgacta ctgttcagat tgaaatcaca ttgaagatgt cactcgaggg gtaccaaaaa     840 aggttttgg atgctgcagt ggcttcgcag gccttgaagt ttggaactt caccttgaaa      900 agtggaagac agtctccata cttctttaac atgggtcttt tcaacaaagc tccattagtg     960
agtcagctgg ctgaatctta tgctcaggcc atcattaaca gcaacctgga gatagacgtt    1020
gtatttggac cagcttataa aggtattcct ttggctgcta ttaccgtgtt gaagttgtac    1080
gagctcggcg gcaaaaaata cgaaaatgtc ggatatgcgt tcaatagaaa agaaaagaaa    1140
gaccacggag aaggtggaag catcgttgga gaaagtctaa agaataaaag agtactgatt    1200
atcgatgatg tgatgactgc aggtactgct atcaacgaag catttgctat aattggagct    1260
gaaggtggga gagttgaagg ttgtattatt gccctagata gatgagac tacaggagat    1320 gactcaaata ccagtgctac ccaggctgtt agtcagagat atggtacccc tgtcttgagt    1380
atagtgacat tggaccatat tgtggcccat tgggcgaaa ctttcacagc agacgagaaa    1440
tctcaaatgg aaacgtatag aaaaaagtat ttgcccaaat aagtatgaat ctgcttcgaa    1500
tgaatgaatt aatccaatta tcttctcacc attatttct tctgtttcgg agctttgggc    1560
acggcggcgg gtggtgcggg ctcaggttcc ctttcataaa cagatttagt acttggatgc    1620
ttaatagtga atggcgaatg caaggaaca atttcgttca tctttaaccc tttcactcgg    1680
ggtacacgtt ctggaatgta cccgccctgt tgcaactcag gtggaccggg caattcttga    1740
actttctgta acgttgttgg atgttcaacc agaaattgtc ctaccaactg tattagtttc    1800
cttttggtct tatattgttc atcgagatac ttcccactct ccttgatagc cactctcact    1860
cttcctggat taccaaaatc ttgaggatga gtcttttcag gctccaggat gcaaggtata    1920
tccaagtacc tgcaagcatc taatatt                                       1947
```

<210> SEQ ID NO 2
<211> LENGTH: 666
<212> TYPE: DNA
<213> ORGANISM: Pichia pastoris

<400> SEQUENCE: 2

```
atgtcactcg aggggtacca aaaaaggttt ttggatgctg cagtggcttc gcaggccttg       60
aagtttggaa ctttcacctt gaaagtggaa agacagtctc catacttctt taacatgggt      120
cttttcaaca agctccatt agtgagtcag ctggctgaat cttatgctca ggccatcatt       180
aacagcaacc tggagataga cgttgtattt ggaccagctt ataaaggtat tcctttggct      240
gctattaccg tgttgaagtt gtacgagctc ggcggcaaaa aatacgaaaa tgtcggatat      300
gcgttcaata gaaagaaaa gaagaccac ggagaaggtg gaagcatcgt tggagaaagt       360
ctaaagaata aaagagtact gattatcgat gatgtgatga ctgcaggtac tgctatcaac      420
gaagcatttg ctataattgg agctgaaggt gggagagttg aaggttgtat tattgcccta      480
gatagaatgg agactacagg agatgactca aataccagtg ctacccaggc tgttagtcag      540
agatatggta cccctgtctt gagtatagtg acattggacc atattgtggc ccatttgggc      600
gaaactttca cagcagacga gaaatctcaa atggaaacgt atagaaaaaa gtatttgccc      660
aaataa                                                               666
```

<210> SEQ ID NO 3

```
<211> LENGTH: 221
<212> TYPE: PRT
<213> ORGANISM: Pichia pastoris

<400> SEQUENCE: 3

Met Ser Leu Glu Gly Tyr Gln Lys Arg Phe Leu Asp Ala Val Ala
 1               5                  10                  15

Ser Gln Ala Leu Lys Phe Gly Thr Phe Thr Leu Lys Ser Gly Arg Gln
            20                  25                  30

Ser Pro Tyr Phe Phe Asn Met Gly Leu Phe Asn Lys Ala Pro Leu Val
                35                  40                  45

Ser Gln Leu Ala Glu Ser Tyr Ala Gln Ala Ile Ile Asn Ser Asn Leu
        50                  55                  60

Glu Ile Asp Val Val Phe Gly Pro Ala Tyr Lys Gly Ile Pro Leu Ala
65                  70                  75                  80

Ala Ile Thr Val Leu Lys Leu Tyr Glu Leu Gly Gly Lys Lys Tyr Glu
                85                  90                  95

Asn Val Gly Tyr Ala Phe Asn Arg Lys Glu Lys Lys Asp His Gly Glu
                100                 105                 110

Gly Gly Ser Ile Val Gly Glu Ser Leu Lys Asn Lys Arg Val Leu Ile
            115                 120                 125

Ile Asp Asp Val Met Thr Ala Gly Thr Ala Ile Asn Glu Ala Phe Ala
130                 135                 140

Ile Ile Gly Ala Glu Gly Gly Arg Val Glu Gly Cys Ile Ile Ala Leu
145                 150                 155                 160

Asp Arg Met Glu Thr Thr Gly Asp Asp Ser Asn Thr Ser Ala Thr Gln
                165                 170                 175

Ala Val Ser Gln Arg Tyr Gly Thr Pro Val Leu Ser Ile Val Thr Leu
            180                 185                 190

Asp His Ile Val Ala His Leu Gly Glu Thr Phe Thr Ala Asp Glu Lys
        195                 200                 205

Ser Gln Met Glu Thr Tyr Arg Lys Lys Tyr Leu Pro Lys
    210                 215                 220

<210> SEQ ID NO 4
<211> LENGTH: 430
<212> TYPE: DNA
<213> ORGANISM: Pichia pastoris

<400> SEQUENCE: 4
aatagaagag tggtaataaa agaagacaaa gcctcgaaac ccgtgccgcc gcccaccacg      60
cccgagtcca agggaaagta tttgtctaaa tcatgaacct acgaattatc acttaccgct     120
tacgtttcct tgttaaagca agtagaaatt gggaaagtga gccccatgtg caagacctta     180
catgggcggg acaacgttga gtccacctgg cccgttaaga acttgaaaga cattgcaaca     240
acctacaagt tggtctttaa caggatggtt gacataatca aggaaaaacc agaatataac     300
aagtagctct atgaagggtg agaggaacta tcggtgagag tgagaaggac ctaatggttt     360
tagaactcct actcagaaaa gtccgaggtc ctacgttcca tataggttca tggacgttcg     420
tagattataa                                                           430

<210> SEQ ID NO 5
<211> LENGTH: 142
<212> TYPE: PRT
<213> ORGANISM: Pichia pastoris

<400> SEQUENCE: 5
```

Ile Leu Asp Ala Cys Arg Tyr Leu Asp Ile Pro Cys Ile Leu Glu Pro
1               5                  10                 15

Glu Lys Thr His Pro Gln Asp Phe Gly Asn Pro Gly Arg Val Arg Val
            20                 25                 30

Ala Ile Lys Glu Ser Gly Lys Tyr Leu Asp Glu Gln Tyr Lys Thr Lys
            35                 40                 45

Arg Lys Leu Ile Gln Leu Val Gly Gln Phe Leu Val Glu His Pro Thr
50                  55                 60

Thr Leu Gln Lys Val Gln Glu Leu Pro Gly Pro Pro Glu Leu Gln Gln
65                  70                 75                 80

Gly Gly Tyr Ile Pro Glu Arg Val Pro Arg Val Lys Gly Leu Lys Met
                85                 90                 95

Asn Glu Ile Val Pro Leu His Ser Pro Phe Thr Ile Lys His Pro Ser
            100                105                110

Thr Lys Ser Val Tyr Glu Arg Glu Pro Glu Pro Ala Pro Pro Ala Ala
            115                120                125

Val Pro Lys Ala Pro Lys Gln Lys Lys Ile Met Val Arg Arg
130                 135                140

<210> SEQ ID NO 6
<211> LENGTH: 668
<212> TYPE: DNA
<213> ORGANISM: Pichia pastoris

<400> SEQUENCE: 6
gatcatggac taaggagttt tatttggacc aagttcatcg tcctagacat tacggaaagg     60
gttctgctcc tcttttttgga aacttttttgg aacctctgag tatgacagct ggtggattg    120
tacccatggt atggcttcct gtgaatttct attttttcta cattggattc accaatcaaa   180
acaaattagt cgccatggct ttttggcttt tgggtctatt tgtttggacc ttcttggaat   240
atgctttgca tagattttttg ttccacttgg actactatct tccagagaat caaattgcat   300
ttaccattca tttcttattg catgggatac accactattt accaatggat aaatacagat   360
tggtgatgcc acctacactt tcattgtac tttgctaccc aatcaagacg ctcgtctttt   420
ctgttctacc atattacatg gcttgttctg gatttgcagg tggattcctg gctatatca   480
tgtatgatgt cactcattac gttctgcatc actccaagct gcctcgttat ttccaagagt   540
tgaagaaata tcatttggaa catcactaca agaattacga gttaggcttt ggtgtcactt   600
ccaaattctg ggacaaagtc tttgggactt atctgggtcc agacgatgtg tatcaaaaga   660
caaattag                                                            668

<210> SEQ ID NO 7
<211> LENGTH: 221
<212> TYPE: PRT
<213> ORGANISM: Pichia pastoris

<400> SEQUENCE: 7

Ser Trp Thr Lys Glu Phe Tyr Leu Asp Gln Val His Arg Pro Arg His
1               5                  10                 15

Tyr Gly Lys Gly Ser Ala Pro Leu Phe Gly Asn Phe Leu Glu Pro Leu
            20                 25                 30

Ser Met Thr Ala Trp Trp Ile Val Pro Met Val Trp Leu Pro Val Asn
            35                 40                 45

Phe Tyr Phe Phe Tyr Ile Gly Phe Thr Asn Gln Asn Lys Leu Val Ala
50                  55                 60

Met Ala Phe Trp Leu Leu Gly Leu Phe Val Trp Thr Phe Leu Glu Tyr

-continued

```
                65                  70                  75                  80
Ala Leu His Arg Phe Leu Phe His Leu Asp Tyr Tyr Leu Pro Glu Asn
                    85                  90                  95

Gln Ile Ala Phe Thr Ile His Phe Leu Leu His Gly Ile His His Tyr
                100                 105                 110

Leu Pro Met Asp Lys Tyr Arg Leu Val Met Pro Pro Thr Leu Phe Ile
                115                 120                 125

Val Leu Cys Tyr Pro Ile Lys Thr Leu Val Phe Ser Val Leu Pro Tyr
                130                 135                 140

Tyr Met Ala Cys Ser Gly Phe Ala Gly Gly Phe Leu Gly Tyr Ile Met
145                 150                 155                 160

Tyr Asp Val Thr His Tyr Val Leu His His Ser Lys Leu Pro Arg Tyr
                165                 170                 175

Phe Gln Glu Leu Lys Lys Tyr His Leu Glu His His Tyr Lys Asn Tyr
                180                 185                 190

Glu Leu Gly Phe Gly Val Thr Ser Lys Phe Trp Asp Lys Val Phe Gly
                195                 200                 205

Thr Tyr Leu Gly Pro Asp Asp Val Tyr Gln Lys Thr Asn
210                 215                 220

<210> SEQ ID NO 8
<211> LENGTH: 54
<212> TYPE: PRT
<213> ORGANISM: Saccharomyces cerevisiae

<400> SEQUENCE: 8

Leu Lys Ser Gly Arg Glu Ser Pro Tyr Phe Phe Asn Leu Gly Leu Phe
1               5                   10                  15

Asn Thr Gly Lys Leu Leu Ser Asn Leu Ala Thr Ala Tyr Ala Ile Ala
                20                  25                  30

Ile Ile Gln Ser Asp Leu Lys Phe Asp Val Ile Phe Gly Pro Ala Tyr
            35                  40                  45

Lys Gly Ile Pro Leu Ala
    50

<210> SEQ ID NO 9
<211> LENGTH: 54
<212> TYPE: PRT
<213> ORGANISM: Saccharomyces cerevisiea

<400> SEQUENCE: 9

Leu Asn Ser Gly Arg Gln Ser Pro Tyr Phe Phe Asn Leu Ser Leu Phe
1               5                   10                  15

Asn Ser Gly Lys Leu Leu Ala Asn Leu Ala Thr Ala Tyr Ala Thr Ala
                20                  25                  30

Ile Ile Gln Ser Glu Leu Lys Phe Asp Val Ile Phe Gly Pro Ala Tyr
            35                  40                  45

Lys Gly Ile Pro Leu Ala
    50

<210> SEQ ID NO 10
<211> LENGTH: 54
<212> TYPE: PRT
<213> ORGANISM: Kluyveromyces lactis

<400> SEQUENCE: 10

Leu Lys Ser Gly Arg Val Ser Pro Tyr Phe Phe Asn Leu Gly Leu Phe
1               5                   10                  15
```

```
Asn Thr Gly Lys Leu Leu Ser Asn Leu Ala Thr Ala Tyr Ala Ile Ala
            20                  25                  30

Ile Ile Gln Ser Glu Leu Lys Phe Asp Val Ile Phe Gly Pro Ala Tyr
            35                  40                  45

Lys Gly Ile Pro Leu Ala
            50

<210> SEQ ID NO 11
<211> LENGTH: 54
<212> TYPE: PRT
<213> ORGANISM: Yarrowia lipolytica

<400> SEQUENCE: 11

Leu Lys Ser Gly Arg Thr Ser Pro Tyr Phe Phe Asn Leu Gly Leu Phe
1               5                   10                  15

Asn Thr Gly Val Ala Leu Ser Thr Val Gly Ala Ser Phe Ala Gln Val
            20                  25                  30

Ile Ile Asn Ser Gly Val Glu Phe Asp Val Ile Phe Gly Pro Ala Tyr
            35                  40                  45

Lys Gly Ile Pro Leu Ala
            50

<210> SEQ ID NO 12
<211> LENGTH: 54
<212> TYPE: PRT
<213> ORGANISM: Schizosaccharomyces pombe

<400> SEQUENCE: 12

Leu Lys Ser Gly Arg Lys Ser Pro Tyr Phe Phe Asn Ser Gly Asn Phe
1               5                   10                  15

Thr His Gly Ala Asp Leu Cys Ala Leu Ala Glu Ala Tyr Ala Glu Thr
            20                  25                  30

Ile Ile Ala Met Asn Val Asp Phe Asp Val Ile Phe Gly Pro Ala Tyr
            35                  40                  45

Lys Gly Ile Ser Leu Ala
            50

<210> SEQ ID NO 13
<211> LENGTH: 58
<212> TYPE: PRT
<213> ORGANISM: Tricoderma reesei

<400> SEQUENCE: 13

Leu Lys Ser Lys Arg Ile Ser Pro Tyr Phe Phe Asn Ala Gly Glu Phe
1               5                   10                  15

His Thr Ala Arg Leu Ala Arg Arg Ile Ala Ser Ala Phe Ala Lys Thr
            20                  25                  30

Ile Ile Glu Ala Gln Glu Lys Ala Gly Leu Glu Phe Asp Ile Val Phe
            35                  40                  45

Gly Pro Ala Tyr Lys Gly Ile Pro Leu Cys
            50                  55

<210> SEQ ID NO 14
<211> LENGTH: 54
<212> TYPE: PRT
<213> ORGANISM: escherichia coli

<400> SEQUENCE: 14

Leu Lys Ser Gly Arg Lys Ser Pro Tyr Phe Phe Asn Ala Gly Leu Phe
1               5                   10                  15
```

```
Asn Thr Gly Arg Asp Leu Ala Leu Leu Gly Arg Phe Tyr Ala Glu Ala
            20                  25                  30

Leu Val Asp Ser Gly Ile Glu Phe Asp Leu Leu Phe Gly Pro Ala Tyr
        35                  40                  45

Lys Gly Ile Pro Ile Ala
        50

<210> SEQ ID NO 15
<211> LENGTH: 54
<212> TYPE: PRT
<213> ORGANISM: Pseudomonas aeroginosa

<400> SEQUENCE: 15

Leu Lys Ser Gly Arg Thr Ser Pro Tyr Phe Phe Asn Ala Gly Leu Phe
1               5                   10                  15

Asp Ser Gly Leu Ala Leu Ala Arg Leu Gly Arg Phe Tyr Ala Glu Ala
            20                  25                  30

Val Ile Asp Ser Gly Ile Asp Phe Asp Val Leu Phe Gly Pro Ala Tyr
        35                  40                  45

Lys Gly Ile Pro Leu Ala
        50

<210> SEQ ID NO 16
<211> LENGTH: 54
<212> TYPE: PRT
<213> ORGANISM: Haemophilus influenzae

<400> SEQUENCE: 16

Leu Lys Ser Gly Arg Lys Ser Pro Tyr Phe Phe Asn Ala Gly Leu Phe
1               5                   10                  15

Asn Thr Gly Ala Asp Leu Ala Arg Leu Gly Glu Phe Tyr Ala Ala Ala
            20                  25                  30

Ile Gln Ala Ser Ala Val Asp Phe Asp Val Val Phe Gly Pro Ala Tyr
        35                  40                  45

Lys Gly Ile Pro Ile Gly
        50

<210> SEQ ID NO 17
<211> LENGTH: 59
<212> TYPE: PRT
<213> ORGANISM: Saccharomyces cerevisiae

<400> SEQUENCE: 17

Tyr Pro Cys Tyr Phe Asp Ile Asn Arg Ser His Lys Glu Gly Arg Arg
1               5                   10                  15

Val Pro Lys Glu Leu Ala Val Glu Asn Pro Leu Ala Lys Thr Met Ala
            20                  25                  30

Asp Ala Val Arg Glu Leu Gly Ile Leu Cys Ile Phe Glu Gly Glu Lys
        35                  40                  45

Cys His Pro Gln Asp Phe Gly Asn Pro Gly Arg
        50                  55

<210> SEQ ID NO 18
<211> LENGTH: 59
<212> TYPE: PRT
<213> ORGANISM: Kluyveromyces lactis

<400> SEQUENCE: 18

Tyr Pro Cys Tyr Phe Asp Thr Arg Arg Thr His Ala Gln Gly Arg Arg
1               5                   10                  15
```

Ala Pro Lys Asp Leu Cys Val Glu Asn Pro Leu Ala Lys Thr Ile Ala
            20                  25                  30

Asp Ala Ala Arg Ser Leu Gly Ile Pro Ser Ile Phe Glu Gly Ser Lys
            35                  40                  45

Thr His Pro Gln Asp Phe Gly Asn Pro Gly Arg
    50                  55

<210> SEQ ID NO 19
<211> LENGTH: 59
<212> TYPE: PRT
<213> ORGANISM: Candida albicans

<400> SEQUENCE: 19

Tyr Pro Cys Tyr Phe Asp Ile Asn Arg Ser His Lys Gln Gly Arg Arg
1               5                   10                  15

Val Ser Ile Asp Arg Ala Val Glu Asn Pro Leu Ala Thr Thr Ile Ser
            20                  25                  30

Asp Ala Cys Arg Arg Leu Gly Leu Pro Val Phe Leu Glu Leu Asp Lys
            35                  40                  45

Thr His Pro Gln Asp Phe Gly Asn Pro Gly Arg
    50                  55

<210> SEQ ID NO 20
<211> LENGTH: 59
<212> TYPE: PRT
<213> ORGANISM: Yarrowia lipolytica

<400> SEQUENCE: 20

Tyr Pro Val Tyr Phe Asp Lys Asn Lys Thr Val Gly Glu Gly Arg Arg
1               5                   10                  15

Val Pro Leu Glu Leu Ala Val Glu Asn Pro Leu Gly Gln Thr Ile Ala
            20                  25                  30

Glu Ala Cys Lys Met Leu Thr Leu Pro Ser Ile Tyr Glu Ala His Lys
            35                  40                  45

Thr His Pro Lys Asp Trp Ala Asn Pro Gly Arg
    50                  55

<210> SEQ ID NO 21
<211> LENGTH: 59
<212> TYPE: PRT
<213> ORGANISM: Neurospora crassa

<400> SEQUENCE: 21

Tyr Pro Cys Tyr Phe Asp Ala Thr Arg Ser Arg Ala Glu Gly Arg Arg
1               5                   10                  15

Val Ser Lys Glu Leu Ala Val Pro Asn Pro Leu Ala Thr Glu Ile Val
            20                  25                  30

Asn Ala Cys Ala Gln Leu Arg Leu Ser Val Val Leu Glu Ala Gly Lys
            35                  40                  45

Leu His Pro Lys Asp Trp Ala Asn Pro Gly Arg
    50                  55

<210> SEQ ID NO 22
<211> LENGTH: 58
<212> TYPE: PRT
<213> ORGANISM: Schizosaccharomyces pombe

<400> SEQUENCE: 22

Tyr Pro Ile Tyr Phe Asp Lys Ser Arg Pro Arg Arg Phe Arg Cys Val
1               5                   10                  15

```
Pro Lys Asp Lys Ala Ile Leu Asn Pro Leu Ala Lys Asn Ile Ala Asp
             20                  25                  30

Val Val Arg Asp Leu Gly Tyr Lys Cys Lys Leu Glu Pro Leu Lys Thr
         35                  40                  45

His Pro Ala Asp Trp Val Asn Pro Gly Arg
     50                  55

<210> SEQ ID NO 23
<211> LENGTH: 35
<212> TYPE: DNA
<213> ORGANISM: Artificial Sequence
<220> FEATURE:
<223> OTHER INFORMATION: Degenerate oligonucleotide primer

<400> SEQUENCE: 23
ttgaagtctg gtagagaatc tccataytty ttyaa                          35

<210> SEQ ID NO 24
<211> LENGTH: 35
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 24
<223> OTHER INFORMATION: n= a, t, g, c
<220> FEATURE:
<221> NAME/KEY: misc_feature
<222> LOCATION: 33
<223> OTHER INFORMATION: n= a, t, g, c

<400> SEQUENCE: 24
tttgatgtta tttttggtcc agcntayaar ggnat                          35

<210> SEQ ID NO 25
<211> LENGTH: 33
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 25
<223> OTHER INFORMATION: n= a, t, g, c
<220> FEATURE:
<221> NAME/KEY: misc_feature
<222> LOCATION: 28
<223> OTHER INFORMATION: n= a, t, g, c

<400> SEQUENCE: 25
agccaatgga ataccttgt aagcnggncc raa                             33

<210> SEQ ID NO 26
<211> LENGTH: 32
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 24
<223> OTHER INFORMATION: n= a, t, g, c
<220> FEATURE:
<221> NAME/KEY: misc_feature
<222> LOCATION: 30
<223> OTHER INFORMATION: n= a, t, g, c

<400> SEQUENCE: 26
agaaaggaag ctaaggatca tggngarggn gg                             32
```

<210> SEQ ID NO 27
<211> LENGTH: 30
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 22
<223> OTHER INFORMATION: n= a, t, g, c

<400> SEQUENCE: 27
accaccttca ccatgatcct tngcytcytt                                30

<210> SEQ ID NO 28
<211> LENGTH: 27
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 19
<223> OTHER INFORMATION: n= a, t, g, c

<400> SEQUENCE: 28
agcagtacca gcagtcatna crtcrtc                                   27

<210> SEQ ID NO 29
<211> LENGTH: 35
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: 27
<223> OTHER INFORMATION: n= a, t, g, c

<400> SEQUENCE: 29
aagagatttc aagttttgta cccadkntay ttyga                          35

<210> SEQ ID NO 30
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 30
gggatatcgg cctttgttga tgcaagtttt acgtggatc                      39

<210> SEQ ID NO 31
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 31
gcgatatcgg tgaaagttcc aaacttcaag gcctgcgaag                     40

<210> SEQ ID NO 32
<211> LENGTH: 40
<212> TYPE: DNA
<213> ORGANISM: Artificial Sequence
<220> FEATURE:
<223> OTHER INFORMATION: Oligonucleotide primer -continued

```
<400> SEQUENCE: 32
gacgcgtcga cggtctttc aacaaagctc cattagtgag                        40

<210> SEQ ID NO 33
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 33
acatgcatgc gccaaaagga gtatggtgtg gagaaccc                         38

<210> SEQ ID NO 34
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 34
ggcgagctcg gcctacccgg ccaaggctga gatcatttgt ccagcttcag a          51

<210> SEQ ID NO 35
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 35
gcccacgtcg acggatccgt ttaaacatcg attggagagg ctgacaccgc tacta      55

<210> SEQ ID NO 36
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 36
cgggatccac tagtatttaa atcatatgtg cgagtgtaca actcttccca catgg      55

<210> SEQ ID NO 37
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 37
ggacgcgtcg acggcctacc cggccgtacg aggaatttct cggatgactc ttttc      55

<210> SEQ ID NO 38
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 38
cgggatccct cgagagatct tttttgtaga aatgtcttgg tgcct                 45

<210> SEQ ID NO 39
<211> LENGTH: 63
```

```
<212> TYPE: DNA
<213> ORGANISM: Artificial Sequence
<220> FEATURE:
<223> OTHER INFORMATION: Oligonucleotide primer

<400> SEQUENCE: 39
ggacatgcat gcactagtgc ggccgccacg tgatagttgt tcaattgatt gaaataggga    60
caa                                                                 63

<210> SEQ ID NO 40
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 40
ccttgctagc ttaattaacc gcggcacgtc cgacggcggc ccacgggtcc ca            52

<210> SEQ ID NO 41
<211> LENGTH: 61
<212> TYPE: DNA
<213> ORGANISM: Artificial Sequence
<220> FEATURE:
<223> OTHER INFORMATION: Oligonucleotide primer

<400> SEQUENCE: 41
ggacatgcat gcggatccct taagagccgg cagcttgcaa attaaagcct tcgagcgtcc    60
c                                                                   61

<210> SEQ ID NO 42
<211> LENGTH: 61
<212> TYPE: DNA
<213> ORGANISM: Artificial Sequence
<220> FEATURE:
<223> OTHER INFORMATION: Oligonucleotide primer

<400> SEQUENCE: 42
gaaccacgtc gacggccatt gcggccaaaa ccttttttcc tattcaaaca caaggcattg    60
c                                                                   61

<210> SEQ ID NO 43
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 43
ctccaatact agtcgaagat tatcttctac ggtgcctgga ctc                     43

<210> SEQ ID NO 44
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 44
tggaaggttt aaacaaagct agagtaaaat agatatagcg agattagaga atg           53

<210> SEQ ID NO 45
<211> LENGTH: 50
<212> TYPE: DNA
<213> ORGANISM: Artificial Sequence
```

```
<220> FEATURE:
<223> OTHER INFORMATION: Oligonucleotide primer

<400> SEQUENCE: 45
aagaattcgg ctggaaggcc ttgtaccttg atgtagttcc cgttttcatc        50

<210> SEQ ID NO 46
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 46
gctctagagg gacttatctg ggtccagacg atgtg                         35

<210> SEQ ID NO 47
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 47
cgggatccgc cgccgtgccc aaagctccga aacag                         35
```

URA5 GENE AND METHODS FOR STABLE GENETIC INTEGRATION IN YEAST

CROSS REFERENCE TO RELATED APPLICATIONS

This patent application is a divisional application of U.S. Ser. No. 12/321,512 filed Jan. 22, 2009 which is a divisional of Ser. No. 10/454,125 filed Jun. 3, 2003 and which claims benefit of U.S. Provisional Application No. 60/471,435 filed May 16, 2003.

FIELD OF THE INVENTION

This invention relates to novel genes isolated in yeast. The invention also relates to plasmids, which are particularly useful for stable genetic integration into the yeast genome. The present invention also relates to novel yeast strains in the expression of heterologous proteins and to methods of generating the novel strains.

BACKGROUND OF THE INVENTION

Yeast strains, such as *Pichia pastoris*, are commonly used for the production of heterologous proteins. *P. pastoris* has become a popular model system for the study of peroxisome biogenesis (Gould et al., *Yeast* 8:613-628 (1992)), autophagy (Tuttle and Dunn, *J. Cell Sci.* 108:25-35 (1995); Sakai et al., *J. Cell Biol.* 141:625-636 (1998)) and the organization and biogenesis of the organelles of the secretory pathway (Rossanese et al., *J. Cell Biol.* 145:69-81 (1999)). The development of simple DNA transformation systems (see Cregg et al., *Mol. Cell. Biol.* 5:3376-3385 (1985)) and the availability of selectable marker genes have been of great importance in conducting the above experiments. Currently, the biosynthetic marker genes ADE1, ARG4, HIS4 and URA3 are used in conjunction with the corresponding auxotrophic host strains to select for transformed cells. Lin Cereghino et al., *Gene* 263:159-169 (2001). The use of dominant selectable markers to identify transformants is also possible, but markers are limited to the Sh ble gene from *Streptoalloteichus hindustanus*, which confers resistance to the drug Zeocin (Higgins et al., *Methods Mol. Biol.* 103:41-53 (1998)), and the blasticidin S deaminase gene from *Aspergillus terreus*, which confers resistance to the drug blasticidin (Kimura et al., *Mol. Gen. Genet.* 242:121-129 (1994)).

Stable integration of cloned DNA segments into the yeast genome through homologous recombination is well known in the art. See e.g., Orr-Weaver et al., *Proc. Natl. Acad. Sci. USA* 78:6364-6358 (1981). More recently, methods have been developed in *S. cerevisiae* to generate yeast strains containing DNA integrated at multiple unlinked sites by homologous recombination using molecular constructs containing the URA3 marker gene. See e.g., Alani et al., *Genetics* 116:541-545 (1987). In this approach, a construct is generated in which the *S. cerevisiae* URA3 gene is flanked by direct repeats of a *Salmonella* hisG DNA. This construct is inserted into a cloned target gene of interest and the linear cassette, containing the complete URA3 gene flanked by direct repeats from hisG and further flanked by 5' and 3' segments from the target gene, is introduced into a Ura3⁻ mutant yeast strain by transformation. Stable integrants arising from homologous recombination at the genomic locus of the target gene linked to the URA3 marker gene are then isolated by selection for growth in the absence of uracil. Excision of the URA3 gene through a recombination event between the flanking hisG direct repeat segments restores uracil auxotrophy (Ura⁻) but leaves behind a disrupted genomic copy of the target gene. Ura⁺ strains of *S. cerevisiae* are unable to grow on medium supplemented with the pyrimidine analog 5-fluoroorotic acid (5-FOA) whereas Ura⁻ cells survive such treatment. Cells lacking the URA3 gene are thus readily identified using a positive counterselection on 5-FOA. Boeke et al., *Mol. Gen. Genet.* 197:345-346 (1984). Through repeated use of the recyclable URA3 marker construct, multiple different genes of interest can be disrupted within a single strain. Similar approaches have been used in other fungi. Wilson et al., *Yeast* 16:65-70 (2000).

Extensive genetic engineering projects, where several genes in parallel have to be expressed and several others have to be eliminated, require the use of counterselectable markers and plasmids for stable genetic integration of heterologous proteins into the host genome. Recently, a new counterselectable marker based on the T-urf13 gene from the mitochondrial genome of male-sterile maize has been described for *P. pastoris*. Soderholm et al., *BioTechniques* 31:306-312 (2001). Toxicity of the T-urf13 gene appears to be a host specific problem, however, as the gene may be conditionally lethal with certain gene disruptions that are otherwise not lethal. In addition, the gene is also toxic in the absence of the counterselecting agent methomyl, therefore, the counterselection step must be performed immediately. In addition, a separate gene is required for the initial positive selection step, and the agent used for the counterselection step, methomyl, is light sensitive and breaks down rapidly in aqueous solutions. The system is therefore more complicated than the URA3 system described above, in which the same gene is responsible both for the initial selection of Ura⁺ prototrophs and for the subsequent counterselection of Ura⁻ auxotrophs. It would be useful to find new marker genes in the yeast pyrimidine biosynthetic pathway in which selection of auxotrophs and counterselection using 5-FOA or similarly acting agents may be used to select and counterselect a single marker gene in multiple rounds of genetic transformation at different loci.

Five structural genes providing six enzymatic steps are responsible for endogenous pyrimidine biosynthesis in *S. cerevisiae*. Montigny et al., *Mol. Gen. Genet.* 215:455-462 (1989). The last two steps in this pathway, the conversion of orotic acid to orotidine 5'-phosphate and the conversion of orotidine 5'-phosphate to uridine 5'-phosphate, are catalyzed by orotate phosphoribosyltransferase (OPRTase) and orotidine-5'-phosphate decarboxylase (OMPdecase). These enzymes are encoded by the URA5 gene and the URA3 gene, respectively. Both genes have been cloned, characterized and used for genetic integration in *S. cerevisiae*, but only the URA3 gene has been cloned in *P. pastoris*.

The *S. cerevisiae* URA5 gene was cloned by complementation of a non-reverting *E. coli* pyrE mutant that was blocked in orotate-phosphoribosyl transferase activity. Montigny et al., *Mol. Gen. Genet.* 215:455-462 (1989). Yeast cells lacking this gene displayed a leaky phenotype, however, indicating that, in *S. cerevisiae*, another protein possesses orotate-phosphoribosyl transferase activity. See Jund and Lacroute, *J. Bacteriol.* 109:196-202 (1972). The URA5 gene has also been identified in *Kluyveromyces lactis*. Bai et al., *Yeast* 15:1393-1398 (1999). The gene order around the URA5 gene has been examined in *S. cerevisiae, K. lactis, C. albicans* and *Y. lipolytica*. Sánchez and Domínguez, *Yeast* 18:807-813 (2001). In all four organisms, the URA5 gene and a gene which functions in the secretory pathway (the SEC65 gene) are arranged adjacent to one another and in the opposite relative orientation.

A selection system based on disrupting the URA3 gene in *P. pastoris* has recently been disclosed. U.S. Pat. No. 6,051, 419. The methods described therein also provide "pop-in" (site-directed integration of the transforming DNA by gene addition) and "pop-out" (recombination between functional and nonfunctional genes resulting in the loss of one of these genes and the URA3 gene) in what is referred to as a "bidirectional selection process." "Pop-in/pop-out" gene replacement using *S. cerevisiae* URA3 is a convenient method because, as described above, the selection marker can be recycled. See Boeke et al., *Meth. Enzymol.* 154:164-175 (1987). *P. pastoris* ura3 auxotrophs, however, grow slowly. U.S. Pat. No. 6,051,419. In addition, because the sequences responsible for homologous recombination in the "popping out" step are the same as those responsible for the "popping in" step in a single-crossover recombination process, the genetic material inserted by "pop-in" is likely to be lost by "pop-out". The method is thus more suitable for generating point mutants or gene disruptions than for stably incorporating expressable heterologous genes of interest into the genome.

Currently available auxotrophic strains of *P. pastoris* suffer the further disadvantage that the respective auxotrophic marker genes have the potential to revert. A high reversion rate decreases the usefulness of auxotrophic strains, because revertant colonies are misidentified as false-positive transformants.

Given the utility of the URA3 selection and counterselection system in *S. cerevisiae* and the limitations on using these and other current methods in other yeast and fungi, the identification of a URA5 gene in *P. pastoris* and the development of a system for selecting stable genetic integration events using URA5 would be useful.

SUMMARY OF THE INVENTION

The present invention provides isolated polynucleotides comprising or consisting of nucleic acid sequences selected from the group consisting of the coding sequences of the *P. pastoris* URA5 gene, a fragment of the *P. pastoris* SEC65 gene and a fragment of the *P. pastoris* SCS7 gene; nucleic acid sequences that are degenerate variants of these sequences; and related nucleic acid sequences and fragments. The invention also provides vectors and host cells comprising these isolated polynucleotides.

The invention further provides isolated polypeptides comprising or consisting of polypeptide sequences selected from the group consisting of sequences encoded by the *P. pastoris* URA5 gene, by a fragment of the *P. pastoris* SEC65 gene and by a fragment of the *P. pastoris* SCS7 gene, and related polypeptide sequences, fragments and fusions. Antibodies that specifically bind to the isolated polypeptides of the invention are also provided.

The invention also provides host cells comprising a disruption, deletion or mutation of a nucleic acid sequence selected from the group consisting of the coding sequence of the *P. pastoris* URA5 gene, a nucleic acid sequence that is a degenerate variant of the coding sequence of the *P. pastoris* URA5 gene and related nucleic acid sequences and fragments, in which the host cells have a reduced activity of the polypeptide encoded by the nucleic acid sequence compared to a host cell without the disruption, deletion or mutation.

The invention further provides methods for the genetic integration of a heterologous nucleic acid sequence in a host cell. These methods comprise the step of disrupting a host gene encoding orotate-phosphoribosyl transferase by introduction of a disrupted, deleted or mutated nucleic acid sequence derived from a sequence selected from the group consisting of the coding sequence of the *P. pastoris* URA5 gene, a nucleic acid sequence that is a degenerate variant of the coding sequence of the *P. pastoris* URA5 gene and related nucleic acid sequences and fragments.

In addition, the invention provides methods for the genetic integration of a heterologous nucleic acid sequence in a host cell lacking orotate-phosphoribosyl transferase activity. These methods comprise the step of introducing a sequence of interest into the host cell in linkage with a sequence encoding orotate-phosphoribosyl transferase activity selected from the group consisting of the coding sequence of the *P. pastoris* URA5 gene, a nucleic acid sequence that is a degenerate variant of the coding sequence of the *P. pastoris* URA5 gene and related nucleic acid sequences and fragments.

BRIEF DESCRIPTION OF THE DRAWINGS

FIG. 1 shows a 1947 bp URA5-containing genomic fragment (Sau3A-Ssp1) of *P. pastoris* (SEQ ID NO:1), including the URA5 coding sequence (SEQ ID NO:2) and its encoded polypeptide (SEQ ID NO:3), the sequence complementary to the 3' fragment of the SEC65 coding sequence (SEQ ID NO:4) and its encoded polypeptide (SEQ ID NO:5), and the 3' fragment of the SCS7 coding sequence (SEQ ID NO:6) and its encoded polypeptide (SEQ ID NO:7).

FIG. 2 shows an alignment of sequences used to design degenerate primers. The URA5-related sequences are URA5 from *S. cerevisiae* (SEQ ID NO:8), URA10 from *S. cerevisiae* (SEQ ID NO:9), and URA5 from *K. lactis* (SEQ ID NO:10), *Y. lipolytica* (SEQ ID NO:11), *S. pombe* (SEQ ID NO:12), *T. reesei* (SEQ ID NO:13), *E. coli* (SEQ ID NO:14), *P. aeruginosa* (SEQ ID NO:15), and *H. influenzae* (SEQ ID NO:16). The URA5 sequence from *P. pastoris* (residues 27-80 of SEQ ID NO:3) is shown for comparison. The SEC65-related sequences are from *S. cerevisiae* (SEQ ID NO:17), *K. lactis* (SEQ ID NO:18), *C. albicans* (SEQ ID NO:19), *Y. lipolytica* (SEQ ID NO:20), *N. crassa* (SEQ ID NO:21), and *S. pombe* (SEQ ID NO:22).

DETAILED DESCRIPTION OF THE INVENTION

Figure 3:
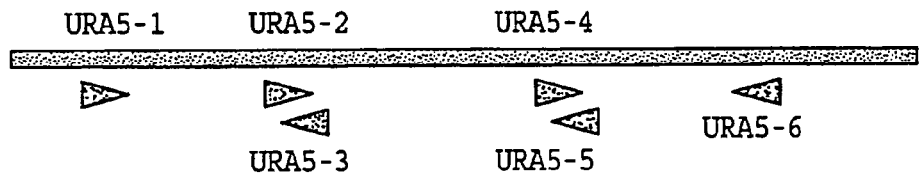
FIG. 3 depicts some of the degenerate oligonucleotides used in cloning of the *P. pastoris* URA5 gene. These oligonucleotides are URA5-1 (SEQ ID NO:23), URA5-2 (SEQ ID NO:24), URA5-3 (SEQ ID NO:25), URA5-4 (SEQ ID NO:26), URA5-5 (SEQ ID NO:27), and URA5-6 (SEQ ID NO:28).

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141

(1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual,* 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique,* 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein, that is not normally produced in the host cell. The methods disclosed herein allow one or more sequences of interest or genes of interest to be stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases and sialyltransferases. Other non-limiting examples include sequences encoding one or more polypeptides having an enzymatic activity, e.g., an enzyme which affects O-glycan synthesis in a host such as protein-mannosyltransferase (PMT) genes. Still other sequences encode proteins of interest such as kringle domains of the human plasminogen, erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II and α-feto proteins.

The term "marker sequence" or "marker gene" refers to a nucleic acid sequence capable of expressing an activity that allows either positive or negative selection for the presence or absence of the sequence within a host cell. For example, the *P. pastoris* URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from *P. pastoris* include ADE1, ARG4, HIS4 and URA3.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such and $^{125}I$, $^{32}P$, $^{35}S$, $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 65% overall sequence homology to its wild-type counterpart. Even more preferred are muteins having at least 70%, 75%, 80%, 85% or 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 65% sequence homology to the wild type protein, more preferred is at least 70% sequence homology. Even more preferred are homologous proteins that exhibit at least 75%, 80%, 85% or 90% sequence homology to the wild type protein. In a yet more preferred embodiment, a homologous protein exhibits at least 95%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are:

Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least twofold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

The present invention provides isolated nucleic acid molecules that include the URA5 gene from *P. pastoris* and variants thereof. The full-length nucleic acid sequence for this gene, which encodes the enzyme orotate-phosphoribosyl transferase (OPRTase, EC 2.4.2.10), has been identified and sequenced as set forth in FIG. 1. Included within the cloned genomic sequence (SEQ ID NO:1) is a coding sequence for orotate-phosphoribosyl transferase (SEQ ID NO:2). The encoded amino acid sequence is also set forth in FIG. 1 (SEQ ID NO:3). The URA5 gene is particularly useful as a reusable, selectable and counterselectable marker.

Provided herein are nucleic acid molecules capable of promoting the stable genetic integration of heterologous genes (i.e. genes of interest) into a host genome. The combination of the URA5 marker and nucleic acids capable of promoting stable genetic integration enables extensive strain modification. It will be readily apparent to a skilled artisan that the repeated use of the methods disclosed herein allows multiple genes to be disrupted in various loci and further allows the insertion at these sites of any gene or genes of interest. Genes inserted by the disclosed approaches become stably integrated at a selected region in the genomic DNA of the host cells.

In one embodiment, the invention provides an isolated nucleic acid molecule having a nucleic acid sequence comprising or consisting of a wild-type *P. pastoris* URA5 coding sequence (SEQ ID NO:2), and homologs, variants and derivatives thereof. The invention also provides a nucleic acid molecule comprising or consisting of a sequence which is a degenerate variant of the wild-type *P. pastoris* URA5 gene. In a further embodiment, the invention provides a nucleic acid molecule comprising or consisting of a sequence which is a variant of the *P. pastoris* URA5 gene having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99%, 99.9% or even higher identity to the wild-type gene.

In another embodiment, the nucleic acid molecule of the invention encodes a polypeptide having the amino acid sequence of SEQ ID NO:3. Also provided is a nucleic acid molecule encoding a polypeptide sequence that is at least 65% identical to SEQ ID NO:3. Typically the nucleic acid molecule of the invention encodes a polypeptide sequence of at least 70%, 75% or 80% identity to SEQ ID NO:3. Preferably, the encoded polypeptide is 85%, 90% or 95% identical to SEQ ID NO:3, and the identity can even more preferably be 98%, 99%, 99.9% or even higher.

In another aspect, the invention provides a fragment of the SEC65 gene from *P. pastoris*. This fragment, which is located downstream from and in the opposite orientation to the URA5 gene, has been identified as set forth in FIG. 1 (SEQ ID NO:4). The amino acid sequence encoded by the SEC65 fragment is also set forth in FIG. 1 (SEQ ID NO:5). Accordingly, the present invention provides isolated nucleic acid molecules that include a wild-type SEC65 gene fragment from *P. pastoris* and homologs, variants and derivatives thereof.

In one embodiment, the invention provides an isolated nucleic acid molecule having a nucleic acid sequence comprising or consisting of a fragment of the wild-type *P. pastoris* SEC65 gene (SEQ ID NO:4), and homologs, variants and derivatives thereof. In an alternative embodiment of the invention, the nucleic acid sequence is a degenerate variant of the *P. pastoris* SEC65 gene fragment.

In a further embodiment of the invention, the nucleic acid sequence is a variant of the *P. pastoris* SEC65 gene fragment having at least 65% identity to the wild-type gene fragment. The nucleic acid sequence can preferably have at least 70%, 75% or 80% identity to the wild-type gene fragment. Even more preferably, the nucleic acid sequence can have 85%, 90%, 95%, 98%, 99%, 99.9% or even higher identity to the wild-type gene fragment.

In another embodiment, the nucleic acid molecule of the invention encodes a polypeptide having the amino acid sequence of SEQ ID NO:5. Also provided is a nucleic acid molecule encoding a polypeptide sequence that is at least 65% identical to SEQ ID NO:5. Typically, the nucleic acid molecule of the invention encodes a polypeptide sequence of at least 70%, 75% or 80% identity to SEQ ID NO:5. Preferably, the encoded polypeptide is 85%, 90% or 95% identical to SEQ ID NO:5, and the identity can even more preferably be 98%, 99%, 99.9% or even higher.

In yet another aspect, the invention provides a fragment of the SCS7 gene from *P. pastoris*. This fragment, which is located upstream from and in the same orientation as the URA5 gene, is identified as set forth in FIG. 1 (SEQ ID NO:6). The amino acid sequence encoded by the SCS7 fragment is also set forth in FIG. 1 (SEQ ID NO:7). The present invention thus provides isolated nucleic acid molecules that include a *P. pastoris* wild-type SCS7 gene fragment and variants thereof.

In one embodiment, the invention provides an isolated nucleic acid molecule having a nucleic acid sequence comprising or consisting of a fragment of the wild-type *P. pastoris* SCS7 gene (SEQ ID NO:6), and homologs, variants and derivatives thereof. In an alternative embodiment of the invention, the nucleic acid sequence is a degenerate variant of the *P. pastoris* SCS7 gene fragment.

In a further embodiment of the invention, the nucleic acid sequence is a variant of the *P. pastoris* SCS7 gene fragment having at least 65% identity to the wild-type gene fragment. The nucleic acid sequence can preferably have at least 70%, 75% or 80% identity to the wild-type gene fragment. Even more preferably, the nucleic acid sequence can have 85%, 90%, 95%, 98%, 99%, 99.9% or even higher identity to the wild-type gene fragment.

In another embodiment, the nucleic acid molecule of the invention encodes a polypeptide having the amino acid sequence of SEQ ID NO:7. Also provided is a nucleic acid molecule encoding a polypeptide sequence that is at least 65% identical to SEQ ID NO:7. Typically, the nucleic acid molecule of the invention encodes a polypeptide sequence of at least 70%, 75% or 80% identity to SEQ ID NO:7. Preferably, the encoded polypeptide is 85%, 90% or 95% identical to SEQ ID NO:7, and the identity can even more preferably be 98%, 99%, 99.9% or even higher.

The invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (*Practical Approach Series*), Schena (ed.), Oxford University Press (1999) (ISBN:

0199637768); *Nature Genet.* 21(1)(suppl):1-60 (1999); *Microarray Biochip Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach (Practical Approach Series)*, Schena (ed.), Oxford University Press (1999) (ISBN: 0199637768); Nature Genet. 21(1)(suppl):1-60 (1999); *Microarray Biochip Tools and Technology*, Schena (ed.), Eaton Publishing Company/Bio-Techniques Books Division (2000) (ISBN: 1881299376), the disclosures of each of which is incorporated herein by reference in its entirety.

In another embodiment, isolated nucleic acid molecules encoding a polypeptide having orotate-phosphoribosyl transferase activity are provided. As is well known in the art, enzyme activities can be measured in various ways. For example, the pyrophosphorolysis of OMP may be followed spectroscopically. Grubmeyer et al., *J. Biol. Chem.* 268: 20299-20304 (1993). Additional examples of substrates useful for the spectroscopic assay of orotate-phosphoribosyl transferase activity are also known in the art. Shostak et al., *Anal Biochem.* 191:365-369 (1990). Alternatively, the activity of the enzyme can be followed using chromatographic techniques, such as by high performance liquid chromatography. Chung and Sloan, *J. Chromatogr.* 371:71-81 (1986). Other methods and techniques may also be suitable for the measurement of enzyme activity, as would be known by one of skill in the art.

The invention also provides recombinant DNA molecules comprising a cassette containing the *P. pastoris* URA5 gene, or a homolog, variant or derivative thereof, flanked by direct repeat sequences. The direct repeat sequences are of sufficient length to mediate efficient homologous recombination, thereby providing a means for deleting the URA5 marker from the host cell in preparation for another round of transformation using the URA5 gene as a positive selection marker. To increase the efficiency of homologous recombination, the direct repeat sequences are preferably at least 200 nucleotides in length (see, e.g., Wilson et al., *Yeast;* 16: 65-70 (2000)). Typically the direct repeat sequences are from around 200 nucleotides to around 1,100 nucleotides, but they may be even longer. In certain preferred embodiments, the direct repeat sequences are derived from hisG segments of *Salmonella*. Alternatively, the direct repeats are obtained from segments of the lacZ reading frame. One of skill in the art will readily appreciate that virtually any other direct repeat sequences may also be used to provide flanking sequences for recombination according to this aspect of the invention.

The URA5-containing cassettes of the invention comprise URA5 sequences with flanking direct repeat sequences which mediate subsequent excision of URA5 sequences from the host. Such URA5 cassettes allow for both selection and counterselection for the URA5 gene activity. The positive selection step is based on relieving auxotrophy to uracil, and the counterselection is based on the acquisition of resistance to 5-FOA in uracil prototrophs. Boeke et al., *Mol. Gen. Genet.* 197:345-346 (1984).

Accordingly, the present invention provides a recombinant nucleic acid molecule comprising a *P. pastoris* URA5 gene flanked by direct repeats (e.g., lacZ-URA5-lacZ, a "URA5 cassette"), which, upon expression, allows for selection and counterselection in a URA5$^-$ host. In a preferred embodiment, yeast transformed with the *P. pastoris* URA5 cassette have integrated the URA5 gene, e.g., into the host genome, at a selected location by homologous recombination between host and recombinant nucleic acid sequences. Preferably, the host is deleted for endogenous URA5 sequences to discourage homologous recombination into an endogenous URA5 locus. The URA5 cassette-containing recombinant nucleic acid molecule preferably comprises sequences which target integration of URA5 and other desired sequences into a select location of the yeast host. As described, such transformants are selected on the basis of conversion from Ura$^-$ to Ura$^+$ phenotypes. The direct repeats flanking the URA5 marker gene then facilitate homologous recombination events which delete the internal URA5 marker. Cells that have undergone such an event revert back to Ura$^-$ and are selected by their ability to grow in the presence of 5-FOA. This method provides for efficient, stable integration of heterologous sequences into a host cell.

There are several advantages to using the *P. pastoris* URA5 marker selection of the present invention. First, this marker gene is relatively small, only about 1 kb. The small size of the marker allows for construction of smaller plasmids. Moreover, the small size should reduce the rate of gene conversion of the auxotrophic marker gene during transformation in a Ura$^-$ host strain which is not deleted for URA5 sequences. This undesirable outcome can account for 10-50% of transformed colonies in the case of the HIS4 marker. Higgins and Cregg, *Meth. Mol. Biol.,* 103:1-15 (1998). A lower rate of gene conversion should increase the fraction of transformants having knock-ins at the desired target site. The *P. pastoris* URA5 marker gene of the invention may be used, moreover, to delete or otherwise disrupt endogenous URA5 host sequences to further reduce the frequency of spontaneous reversion and hence false positive background colonies.

The isolated nucleic acid molecules of the instant invention may additionally include a sequence or gene of interest. As described above, a sequence or gene of interest typically encodes a protein that is not normally produced in the host cell. In a preferred embodiment, yeast transformed with the sequence or gene of interest have stably integrated the sequence or gene of interest, e.g., into the host genome, at a selected location by homologous recombination between host and recombinant nucleic acid sequences. The sequence or gene of interest may be preferably linked to one or more expression control sequences, so that the protein encoded by the sequence can be expressed under appropriate conditions in host cells that contain the isolated nucleic acid molecule.

The invention additionally provides isolated nucleic acid molecules encoding a fragment of the *P. pastoris* SEC65 protein. The *S. cerevisiae* homolog of this protein is related to mammalian SRP19, a subunit of the signal recognition particle, and is thought to have similar function. Hann et al., *Nature* 356:532-533 (1992); Stirling and Hewitt, *Nature* 356: 534-537 (1992). Mutations in the *S. cerevisiae* SEC65 gene can cause temperature-sensitive cell growth and defects in the translocation of several secreted and membrane-bound proteins. The *S. cerevisiae* SEC65 protein is required for the stable association of another subunit, SRP54p, with the signal recognition particle. Id. Overexpression of SRP54p suppresses both growth and protein translocation defects in cells carrying a temperature-sensitive defect in the SEC65 gene. Nucleic acid molecules encoding a fragment of the *P. pastoris* SEC65 gene can be used to identify the full-length gene and can further be used to probe the expression and functional activity of the encoded protein. Such activities may include structural and functional roles in the P. pastoris signal recognition particle and related effects on protein translocation across the endoplasmic reticulum. A shared extended domain structure among fungal SEC65-encoded proteins and the ability of truncation mutants of S. cerevisiae SEC65 to complement conditional lethal mutants in this gene (Regnacq et al., Mol Microbiol 29:753-762 (1998)) indicate that polypeptides encoded by a fragment of the P. pastoris SEC65 gene may provide similar utility.

The invention further provides isolated nucleic acid molecules encoding a fragment of the P. pastoris SCS7 protein. Mutants of S. cerevisiae that lack the S. cerevisiae homolog of SCS7 fail to accumulate an inositolphosphorylceramide species, IPC-C, which is the predominant form found in wild-type cells. Dunn et al., Yeast 14:311-321 (1998). Instead, these mutants accumulate an IPC-B species believed to be unhydroxylated on the amide-linked C26-fatty acid. In addition, elimination of the SCS7 gene suppresses the $Ca^{2+}$-sensitive phenotype of mutations in CSG1 and CSG2, genes required for mannosylation of IPC-C. Id. Accumulation of IPC-C in cells carrying these mutations renders the cells $Ca^{2+}$-sensitive. The full-length S. cerevisiae SCS7 gene encodes a protein that contains both a cytochrome b5-like domain and a domain that resembles the family of cytochrome b5-dependent enzymes that use iron and oxygen to catalyse desaturation or hydroxylation of fatty acids and sterols. Id. The encoded protein is therefore likely to be the enzyme that hydroxylates the C26-fatty acid of IPC-C. Effects of mutations in the SCS7 gene on the lipid composition of a cell can be measured as described in Haak et al., J. Biol. Chem. 272:29704-29710 (1997), which is incorporated by reference herein in its entirety.

The isolated nucleic acid molecules encoding a fragment of the P. pastoris SCS7 protein of the present invention can be used to identify and characterize the full-length form of the SCS7 gene. The isolated nucleic acid molecules of the invention can also be used to measure expression of the SCS7 gene and to further characterize the structure and function of this gene and its encoded protein and the effects of alterations in this gene on cellular metabolism.

Degenerate Oligonucleotides Useful for Cloning of P. pastoris URA5

In another embodiment, degenerate oligonucleotides useful in the isolation of the P. pastoris URA5 gene are provided. These oligonucleotides are capable of amplifying different portions of the P. pastoris URA5 gene. They can also bind to and amplify portions of the S. cerevisiae URA10 gene. That the oligonucleotides only amplify the URA5 gene in P. pastoris suggests that this organism does not posses the URA10 gene. The oligonucleotides anneal to positions of the URA5 gene as shown in FIG. 3. Such oligonucleotides are also useful in hybridization and amplification experiments.

Vectors

Also provided are vectors, including expression vectors, which comprise the above nucleic acid molecules of the invention, as described further herein. In a first embodiment, the vectors include the isolated nucleic acid molecules described above. In an alternative embodiment, the vectors of the invention include the above-described nucleic acid molecules operably linked to one or more expression control sequences. The vectors of the instant invention may thus be used to express a polypeptide having orotate-phosphoribosyl transferase activity.

The vectors of the invention may also include an element which ensures that they are stably maintained at a single copy in each cell (e.g., a centromere-like sequence such as "CEN").

Alternatively, the autonomously replicating vector may optionally comprise an element which enables the vector to be replicated to higher than one copy per host cell (e.g., an autonomously replicating sequence or "ARS"). Methods in Enzymology, Vol. 350: Guide to yeast genetics and molecular and cell biology, Part B., Guthrie and Fink (eds.), Academic Press (2002).

In a preferred embodiment of the invention, the vectors are non-autonomously replicating, integrative vectors designed to function as gene disruption or replacement cassettes. An example of an integrative vector of this type comprises at least at portion of a heterologous target gene linked to P. pastoris orotate-phosphoribosyl transferase ("OPT")-encoding sequences which are preferably flanked by direct repeat sequences. The vectors thus allow the targeted integration of the sequences to be selected for by the expression of OPT activity in cells carrying the integrated vectors. Subsequent excision of the OPT-encoding sequences is facilitated by the flanking direct repeat sequences.

In other embodiments, the integrative vectors of the invention may include additionally heterologous sequences encoding proteins having desirable properties, e.g., those encoding glycosylation enzymes, so that the desired sequences can be introduced into the host cell genome as a result of the integration. These sequences remain in the host cell genome even after the OPT-encoding sequences have been deleted by recombination between flanking direct repeat sequences.

Isolated Polypeptides

According to another aspect of the invention, isolated polypeptides (including muteins, allelic variants, fragments, derivatives, and analogs) encoded by the nucleic acid molecules of the invention are provided. In one embodiment, the isolated polypeptide comprises the polypeptide sequence corresponding to SEQ ID NOs:3, 5 or 7. In an alternative embodiment of the invention, the isolated polypeptide comprises a polypeptide sequence at least 65% identical to SEQ ID NOs:3, 5 or 7. Preferably the isolated polypeptide of the invention has at least 70%, 75% or 80% identity to SEQ ID NOs:3, 5 or 7. More preferably, the identity is 85%, 90% or 95%, but the identity to SEQ ID NOs:3, 5 or 7 can be 98%, 99%, 99.9% or even higher.

According to other embodiments of the invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include heterologous sequences designed to facilitate purification and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cells

In another aspect of the invention, host cells transformed with the nucleic acid molecules or vectors of the invention, and descendants thereof, are provided. In some embodiments of the invention, these cells carry the nucleic acid sequences of the invention on vectors, which may but need not be freely replicating vectors (see below). In other embodiments of the invention, the nucleic acids have been integrated into the genome of the host cells. In a preferred embodiment, the host cells of the invention have been mutated by recombination with a disruption, deletion or mutation of the isolated nucleic acid of the invention so that the activity of orotate-phosphoribosyl transferase activity in the host cell is reduced compared to a host cell lacking the mutation. The host cell of the invention is preferably *Pichia pastoris* or *Pichia methanolica*, but other host cells, especially yeast cells, are also encompassed within the scope of the invention.

In other embodiments of the invention, host cells defective in orotate-phosphoribosyl transferase activity are used to integrate one or more sequences or genes of interest into the host cell genome using nucleic acid molecules and/or methods of the invention. In some embodiments, the sequences or genes of interest are integrated so as to disrupt an endogenous gene of the host cell. Cells containing the integration are identified by the recovery of uracil prototrophy due to the concomitant integration of a gene encoding *P. pastoris* orotate-phosphoribosyl transferase. In a further embodiment of the invention, uracil auxotrophs of the modified host cells are provided by selection of cells in which the *P. pastoris* orotate-phosphoribosyl transferase gene has been excised by homologous recombination.

Antibodies

In another aspect, the invention provides isolated antibodies, including fragments and derivatives thereof, that bind specifically to the isolated polypeptides and polypeptide fragments of the present invention or to one or more of the polypeptides encoded by the isolated nucleic acids of the present invention. The antibodies of the present invention may be specific for linear epitopes, discontinuous epitopes or conformational epitopes of such polypeptides or polypeptide fragments, either as present on the polypeptide in its native conformation or, in some cases, as present on the polypeptides as denatured, as, e.g., by solubilization in SDS. Among the useful antibody fragments provided by the instant invention are Fab, Fab', Fv, F(ab')$_2$, and single chain Fv fragments.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies of the present invention will discriminate over adventitious binding to unrelated polypeptides by at least two-fold, more typically by at least 5-fold, typically by more than 10-fold, 25-fold, 50-fold, 75-fold, and often by more than 100-fold, and on occasion by more than 500-fold or 1000-fold.

Typically, the affinity or avidity of an antibody (or antibody multimer, as in the case of an IgM pentamer) of the present invention for a polypeptide or polypeptide fragment of the present invention will be at least about $1 \times 10^{-6}$ M, typically at least about $5 \times 10^{-7}$ M, usefully at least about $1 \times 10^{-7}$ M, with affinities and avidities of $1 \times 10^{-8}$ M, $5 \times 10^{-9}$ M, $1 \times 10^{-10}$ M and even stronger proving especially useful.

The isolated antibodies of the present invention may be naturally-occurring forms, such as IgG, IgM, IgD, IgE, and IgA, from any mammalian species. For example, antibodies are usefully obtained from species including rodents—typically mouse, but also rat, guinea pig, and hamster—lagomorphs, typically rabbits, and also larger mammals, such as sheep, goats, cows, and horses. The animal is typically affirmatively immunized, according to standard immunization protocols, with the polypeptide or polypeptide fragment of the present invention.

Virtually all fragments of 8 or more contiguous amino acids of the polypeptides of the present invention may be used effectively as immunogens when conjugated to a carrier, typically a protein such as bovine thyroglobulin, keyhole limpet hemocyanin, or bovine serum albumin, conveniently using a bifunctional linker. Immunogenicity may also be conferred by fusion of the polypeptide and polypeptide fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. See, e.g., Tam et al., *Proc. Natl. Acad. Sci. USA* 85:5409-5413 (1988); Posnett et al., *J. Biol. Chem.* 263, 1719-1725 (1988).

Protocols for immunization are well-established in the art. Such protocols often include multiple immunizations, either with or without adjuvants such as Freund's complete adjuvant and Freund's incomplete adjuvant. Antibodies of the present invention may be polyclonal or monoclonal, with polyclonal antibodies having certain advantages in immunohistochemical detection of the proteins of the present invention and monoclonal antibodies having advantages in identifying and distinguishing particular epitopes of the proteins of the present invention. Following immunization, the antibodies of the present invention may be produced using any art-accepted technique. Host cells for recombinant antibody production—either whole antibodies, antibody fragments, or antibody derivatives—can be prokaryotic or eukaryotic. Prokaryotic hosts are particularly useful for producing phage displayed antibodies, as is well known in the art. Eukaryotic cells, including mammalian, insect, plant and fungal cells, are also useful for expression of the antibodies, antibody fragments, and antibody derivatives of the present invention. Antibodies of the present invention can also be prepared by cell free translation.

The isolated antibodies of the present invention, including fragments and derivatives thereof, can usefully be labeled. It is, therefore, another aspect of the present invention to provide labeled antibodies that bind specifically to one or more of the polypeptides and polypeptide fragments of the present invention. The choice of label depends, in part, upon the desired use. In some cases, the antibodies of the present invention may usefully be labeled with an enzyme. Alternatively, the antibodies may be labeled with colloidal gold or with a fluorophore. For secondary detection using labeled avidin, streptavidin, captavidin or neutravidin, the antibodies of the present invention may usefully be labeled with biotin. When the antibodies of the present invention are used, e.g., for Western blotting applications, they may usefully be labeled with radioisotopes, such as $^{33}$P, $^{32}$P, $^{35}$S, $^{3}$H and $^{125}$I. As would be understood, use of the labels described above is not restricted to any particular application.

Methods for the Genetic Integration of Nucleic Acid Sequences: Disruption of a Host Gene Encoding Orotate-Phosphoribosyl Transferase According to another embodiment of the instant invention, a method for the genetic integration of a heterologous nucleic acid sequence into the genome of a host cell is provided. In one aspect of this embodiment, a host gene encoding orotate-phosphoribosyl transferase is disrupted by the introduction of a disrupted, deleted or otherwise mutated nucleic acid sequence derived from the *P. pastoris* URA5 gene disclosed herein. Accordingly, disrupted host cells having a point mutation, rearrangement, insertion or preferably a deletion (including a "marked deletion", in which a heterologous selectable sequence has replaced the deleted URA5 sequence) are provided. Host cells disrupted in the URA5 gene and consequently lacking in orotate-phosphoribosyl transferase activity serve as suitable hosts for further embodiments of the invention in which heterologous sequences may be introduced into the host cell genome by targeted integration.

Methods for the Genetic Integration of Nucleic Acid Sequences: Introduction of a Sequence of Interest in Linkage with a Marker Sequence In another aspect of the instant invention, a heterologous nucleic acid sequence is introduced into a yeast host cell lacking orotate-phosphoribosyl transferase (OPT) activity (i.e., Ura5⁻). The heterologous nucleic acid sequences introduced using this method are linked to a nucleic acid sequence that encodes the *P. pastoris* OPT activity, preferably on a vector. Upon transformation of the vector into competent Ura5⁻ host cells, cells containing heterologous sequences linked to the OPT-encoding sequences of the invention may be selected based on their ability to grow in the absence of added uracil.

In one embodiment, the method comprises the step of introducing into a competent Ura5⁻ host cell an autonomously replicating vector which is passed from mother to daughter cells during cell replication. The autonomously replicating vector comprises heterologous nucleic acid sequences of interest linked to *P. pastoris* OPT-encoding sequences and optionally comprises an element which ensures that it is stably maintained at a single copy in each cell (e.g., a centromere-like sequence such as "CEN"). In another embodiment, the autonomously replicating vector may optionally comprise an element which enables the vector to be replicated to higher than one copy per host cell (e.g., an autonomously replicating sequence or "ARS").

In a preferred embodiment, the vector is a non-autonomously replicating, integrative vector which is designed to function as a gene disruption or replacement cassette. An integrative vector of the invention comprises one or more regions comprising "target gene sequences" (sequences which can undergo homologous recombination with sequences at a desired genomic site in the host cell) linked to *P. pastoris* OPT-encoding sequences of the invention which are preferably flanked by direct repeat sequences (see below). The OPT-encoding sequences may be adjacent to the target gene sequences (e.g., a gene replacement cassette) or may be engineered to disrupt the target gene sequences (e.g., a gene disruption cassette). The presence of target gene sequences in the replacement or disruption cassettes targets integration of the cassette to specific genomic regions in the host by homologous recombination.

In a preferred method of the invention, a host gene that encodes an undesirable activity, (e.g., an enzymatic activity) may be mutated (e.g., interrupted) by targeting a *P. pastoris* OPT-encoding replacement or disruption cassette of the invention into the host gene by homologous recombination. In a preferred embodiment, an undesired glycosylation enzyme activity (e.g., an initiating mannosyltransferase activity such as OCH1) is disrupted in the host cell to alter the glycosylation of polypeptides produced in the cell.

Preferably, the target gene replacement or disruption cassette of the invention further comprises direct repeat sequences flanking the *P. pastoris* orotate-phosphoribosyl transferase gene. The properties of such direct repeat sequences have already been described. After targeted integration of the cassette into the host cell genome and selection of integrants for growth in the absence of uracil, the direct repeat sequences flanking the orotate-phosphoribosyl transferase gene promote the excision of the OPT-encoding gene out of the host genome. Cells lacking orotate-phosphoribosyl transferase activity are conveniently counterselected for their ability to grow in medium containing 5-FOA. One of skill in the art would appreciate, however, that other means may be used to counterselect for cells lacking orotate-phosphoribosyl transferase activity. Because the cells obtained from the counterselection step lack orotate-phosphoribosyl transferase activity, the same *P. pastoris* OPT-encoding nucleic acid sequence may be used in repeated gene disruption events according to this aspect of the invention.

In yet a further embodiment of the invention, a gene encoding a heterologous protein is engineered in linkage to the *P. pastoris* URA5 gene within the gene replacement or disruption cassette. In a preferred embodiment, the cassette is integrated into a locus of the host genome which encodes an undesirable activity, such as an enzymatic activity. For example, in one preferred embodiment, the cassette is integrated into a host gene which encodes an initiating mannosyltransferase activity such as the OCH1 gene. In a more preferred embodiment, the cassette further comprises one or more genes encoding desirable glycosylation enzymes, including but not limited to mannosyltransferases, N-acetylglucosaminyltransferases (GnTs), UDP-N-acetylglucosamine transporters, galactosyltransferases (GalTs), sialyltransferases (STs) and protein-mannosyltransferases (PMTs). In another preferred embodiment, the cassette comprises one or more genes encoding useful therapeutic proteins, e.g., kringle domains of the human plasminogen, erythropoietin, cytokines such as, but not limited to, interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II and α-feto proteins. The engineered cassette is useful for "knocking-in" genes encoding such glycosylation enzymes and other sequences of interest in strains of yeast cells to produce glycoproteins with human-like glycosylations and other useful proteins of interest. Representative methods for producing human-like glycoproteins are described in WO 02/00879 and are incorporated by reference herein.

The following examples are for illustrative purposes and are not intended to limit the scope of the invention.

Example 1

General Materials and Methods

*Escherichia coli* strain DH5α (Invitrogen, Carlsbad, Calif.) was used for recombinant DNA work. *P. pastoris* strains NRRL Y-11430 (wild-type) and JC308 (ade1 arg4 his4 ura3) (Lin Cereghino et al., *Gene* 263:159-169 (2001)) were used for construction of yeast strains. PCR reactions were performed according to supplier recommendations using either ExTaq (TaKaRa, Madison, Wis.), Taq Poly (Promega, Madison, Wis.) or Pfu Turbo (Stratagene, Cedar Creek, Tex.). Restriction and modification enzymes were from New England Biolabs (Beverly, Mass.) or Promega.

PCR analysis of the modified yeast strains was as follows. A single colony was resuspended in 100 µl breaking buffer (100 mM NaCl, 10 mM Tris, pH 8.0, 1 mM EDTA). After addition of 100 mg of acid washed glass beads and 100 µl of phenol-chloroform, the solution was vortexed for 1 min. The mixture was then centrifuged for 5 min at full speed in a microcentrifuge, the supernatant recovered, and the genomic DNA was precipitated by addition of 1 ml ice cold ethanol. Following a wash with 70% ethanol, the pellet was resuspended in 10 µl breaking buffer, and 0.5 to 1 µl were used for PCR analysis.

Cloning of the *P. pastoris* URA5 Gene

Several strategies may be used for cloning and identifying the *P. pastoris* URA5 gene. A preferred method involves using the sequence homology of the existing *S. cerevisiae* URA5 gene in combination with conservation of gene order in a variety of yeast species. Two genes, URA5 and SEC65, are located adjacent to one another in opposite orientations in at least four yeast species: *S. cerevisiae, K. lactis, C. albicans* and *Y. lipolytica.* Sánchez and Domínguez, *Yeast* 18:807-813 (2001). Protein sequences encoded by each of these genes are known in these and other microorganisms (FIG. 2), and these sequences were used to design degenerate primers, e.g., using the CODEHOP strategy. Rose et al., *Nucleic Acids Res.* 26:1628-1635 (1998). Two such primers, designated URA5-1 (FIG. 3) (SEQ ID NO:23) and Sec65-1 (AA-GAGATTTCAAGTTTTGTACCCADKNTAYTTYGA) (SEQ ID NO:29), were used to amplify a 1.1 kb DNA fragment from *P. pastoris* genomic DNA. URA5-1 is on the top strand starting from amino acid 27. This PCR fragment was then cloned into the pCR2.1-TOPO vector (Invitrogen, Carlsbad, Calif.) and sequenced.

The 1100 bp fragment generated by PCR shows high homology on one end to URA5 of *S. cerevisiae* and on the other end to SEC65 genes from *S. cerevisiae, K. lactis, Y. lipolytica,* and *S. pombe.* The derived nucleotide sequence was used to search the partial genomic sequence of *P. pastoris,* as provided by Integrated Genomics, Inc. (Chicago, Ill.). Results of this search identified an overlapping DNA fragment that includes an additional 0.9 kb DNA sequence adjacent to the primer site. Within this sequence is the predicted initiation codon for protein translation. The predicted initiation codon is preceded by about 150 nucleotides of upstream regulatory sequences (including promotor sequences) and about 0.7 kb of the 3' region of a gene with high homology to *S. cerevisiae* SCS7 (FIG. 1). The protein sequence derived by translation of the *P. pastoris* URA5 gene shows about 64% identity and about 78% similarity to the URA5 gene from *S. cerevisiae,* and also displays high homology to URA5 genes from other species. The complete 1947 bp fragment is shown in FIG. 1.

Cloning of *P. pastoris* URA5 Using Alternative Degenerate Oligonucleotides

Degenerate primers were designed using the CODEHOP strategy. Rose et al., *Nucleic Acids Res.* 26:1628-1635 (1998). URA5-1 (SEQ ID NO:23) is a degenerate form of the coding strand, starting from the codon encoding amino acid 27. URA5-2 (SEQ ID NO:24) is a degenerate form of the coding strand starting from the codon encoding amino acid 66. URA5-3 (SEQ ID NO:25) is the partial complement of URA5-2. URA5-4 (SEQ ID NO:26) is a degenerate form of the coding strand, starting from the codon encoding amino acid 105. URA5-5 (SEQ ID NO:27) is the partial complement of URA5-4. URA5-6 (SEQ ID NO:28) is a degenerate form of the non-coding strand, designed to hybridize to the segment of the coding strand starting at the codon encoding amino acid 130. The sequence of and positions within URA5 bound by the oligonucleotides are illustrated in FIG. 3.

Example 2

Disruption of the *P. pastoris* URA5 Gene

The cloned URA5 gene, together with gene-specific primers, may be used to generate a construct to disrupt the URA5 gene from the genome of *P. pastoris*. Host cells with a disrupted URA5 gene were created using a *P. pastoris* URA5 disruption cassette as follows.

Figure 5:
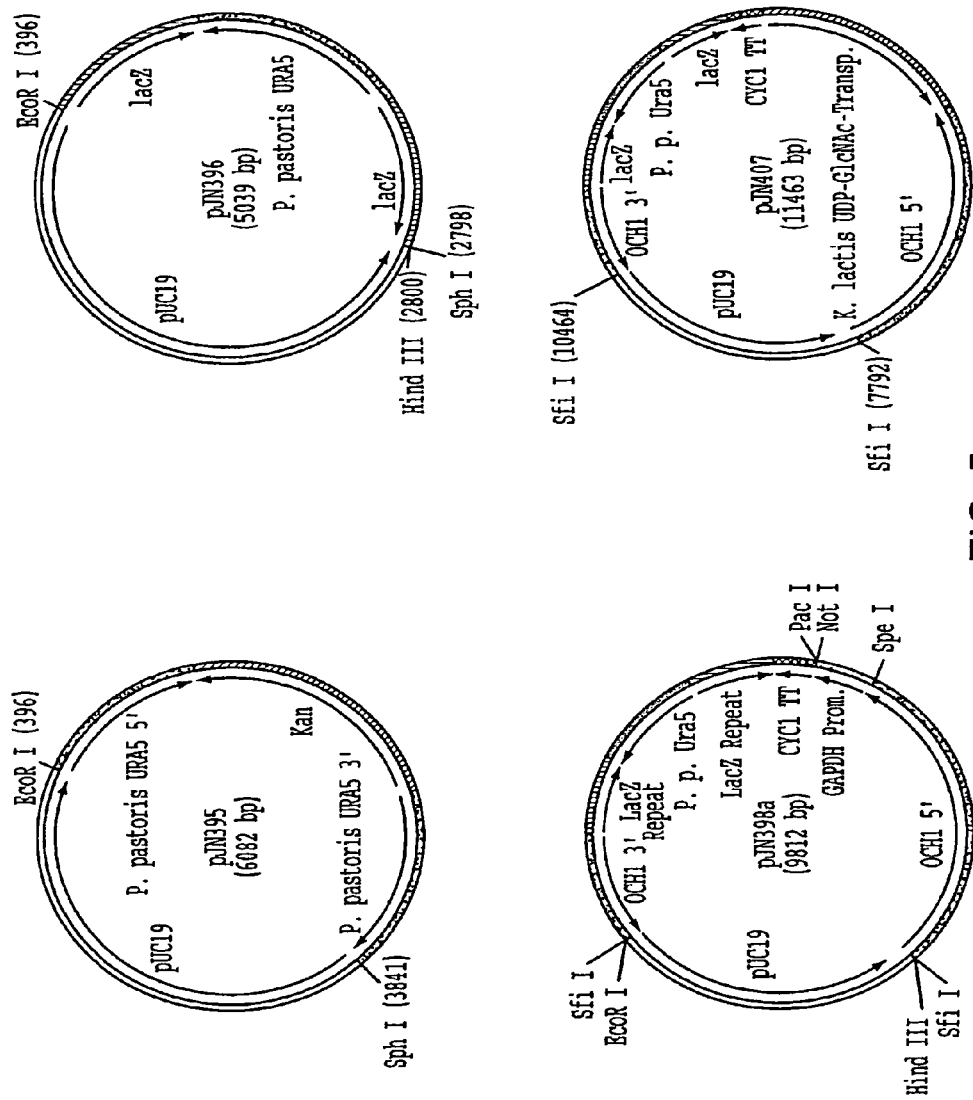
FIG. 5 shows restriction maps of plasmid pJN395 (including a *P. pastoris* URA5 disruption cassette marked with a kanamycin-resistance gene); plasmid pJN396 (including the *P. pastoris* URA5 gene flanked by lacZ direct repeats); plasmid pJN398 (including a recyclable URA5 cassette, which may be used to knock out an OCH1 locus); and plasmid pJN407 (including a *P. pastoris* URA5-*K. lactis* UDP-GlcNAc Transporter cassette, which may be used for stable integration into an OCH1 locus).

A 1.5 kb SacI, XbaI fragment containing the kanamycin-resistance gene of transposon Tn903 was excised from plasmid pUG6 (Güldener et al., *Nucleic Acids Res.* 24:2519-2524 (1996)) and cloned into the SacI, XbaI sites of pUC19 (New England Biolabs, Beverly, Mass.) resulting in pJN374. Oligonucleotides Ura5-55 (GGGATATCG GCCTTTGTTGAT-GCAAGTTTTACGTGGATC) (SEQ ID NO:30) and Ura5-53p (GCGATATCGGTGAAAGTTCCAAACTTCAAGG CCTGCGAAG) (SEQ ID NO:31) were used to amplify a region upstream of the URA5 ATG using *P. pastoris* genomic DNA as a template and Pfu Turbo DNA polymerase. The resulting DNA fragment was cut with EcoRV and cloned into the EcoICRI site of pJN374. The resulting plasmid was then digested with SalI and SphI. A DNA fragment corresponding to part of the coding sequence and the 3' region of the URA5 gene was amplified using oligonucleotides Ura5-35P (GACGC GTCGACGGTCTTTTCAACAAAGCTCCATTAGTGAG) (SEQ ID NO:32) and Ura5-33 (ACAT GCATGCGCCAAAAGGAGTATGGTGTGGAGAACCC) (SEQ ID NO:33). This fragment was inserted into the cut plasmid to create pJN395 (FIG. 5). In this plasmid, codons 27 to 39 of the *P. pastoris* URA5 gene have been replaced by the kanamycin-resistance gene.

Following digestion of pJN395 with EcoRI and SphI, the linearized disruption cassette was transformed into *P. pastoris* wild type strain NRRL Y-11430 (ATCC 76273) by electroporation, and the cells were plated onto YPD plates (*Methods in Enzymology, Vol. 350: Guide to yeast genetics and molecular and cell biology*, Part B., Guthrie and Fink (eds.), Academic Press (2002)) containing 300 mg/l Geneticin (Invitrogen, Carlsbad, Calif.). After 4 days of incubation at 30° C., approximately 10,000 clones were replicated onto plates containing 5-FOA (1.4% Yeast Nitrogen Base, 2% Dextrose, 0.2 g/l Uracil, 1 g/l 5-FOA, 4 mg/l Biotin, 1.5% Agar) and incubated for 7 days at 30° C. Colonies resistant to 5-FOA (240 colonies) were restreaked once on 5-FOA plates and then patched onto YPD and Ura dropout plates (*Methods in Enzymology, Vol. 350: Guide to yeast genetics and molecular and cell biology*, Part B., Guthrie and Fink (eds.), Academic Press (2002)). Cells that failed to grow on Ura dropout plates but that were able to grow on YPD (205 of the original 240 resistant colonies) were then amplified in liquid YPD. Approximately $10^8$ cells of each were plated onto single Ura dropout plates to check for revertants. Thirteen clones gave rise to colonies on the Ura dropout plates and were not examined further. The other clones were unable to revert spontaneously. Based on the most robust growth on YPD and 5-FOA, thirty-one clones were picked and examined by colony PCR, of which, thirty were found to be kanamycin-marked URA5 knockouts. To confirm that the genomic URA5 gene in these strains was disrupted with the kanamycin-resistance gene, one of the colony PCR reactions was digested with either BglII or XbaI. A strain displaying the expected restriction pattern (fragments of 2.35 kb and 1.05 kb) was designated YJN165.

Example 3

Construction of a Set of Vectors for the Stable Genetic Modification of P. pastoris A set of vectors useful for stable gene replacement in Pichia pastoris was constructed as described below. Based on the high copy vector pUC19 (Yanisch-Perron et al., Gene 33:103-119 (1985)), a set of modular plasmids was assembled that, after a few simple subcloning steps, may be used to replace any P. pastoris gene with a heterologous gene of interest under the control of the strong P. pastoris GAPDH promotor. Plasmid pJN266 (FIG. 4) consists of two fragments homologous to the 5' and 3' regions of the P. pastoris KEX1 gene. These segments flank a P. pastoris GAPDH promotor, a S. cerevisiae CYC1 transcriptional terminator expression cassette ("CYC1 TT") and a S. cerevisiae URA3 auxotrophic marker cassette. All regions of this plasmid are flanked by multiple restriction sites and can be individually replaced. The expression cassette contains a multiple cloning site for the insertion of heterologous genes.

Two reusable auxotrophic marker cassettes were constructed based on the approach described by Lu et al., Appl. Microbiol. Biotechnol. 49:141-146 (1998) and Alani et al., Genetics 116:541-545 (1987), using direct repeats from segments of the lacZ reading frame as recombination sites. As counterselectable auxotrophic markers, a 2 kb DNA fragment containing the P. pastoris URA3 gene or a 1 kb fragment harboring the P. pastoris URA5 gene were used. Both marker cassettes were then inserted into a P. pastoris OCH1 knockout plasmid. The P. pastoris URA5-containing plasmid was then modified further to generate a plasmid that includes the heterologous gene for the UDP-N-acetylglucosamine transporter of K. lactis.

Methods

The first step in plasmid construction involved creating a set of universal plasmids containing DNA regions of the KEX1 gene of P. pastoris (Boehm et al., Yeast 15:563-572 (1999)) as space holders for the 5' and 3' regions of the genes to be knocked out. The plasmids also contained the S. cerevisiae URA3 gene, flanked by bacterial direct repeat sequences (Alani et al., Genetics 116: 541-545 (1987)) as a space holder for the auxotrophic markers and an expression cassette with a multiple cloning site for insertion of a foreign gene.

A 0.9-kb fragment of the P. pastoris KEX1-5' region was amplified by PCR using primers Kex 55 (GGC GAGCTCGGCCTACCCGGCCAAGGCTGAGATCATTT GTCCAGCTTC AGA) (SEQ ID NO:34) and Kex 53 (GC-CCACGTCGACGGATCCGTTTAAACATCGATTGGAG AGGCTGACACC GCTACTA) (SEQ ID NO:35) with P. pastoris genomic DNA as a template. The amplified fragment was cloned into the SacI, SalI sites of pUC19 (New England Biolabs, Beverly, Mass.). The resulting plasmid was cut with BamHI and SalI. A 0.8-kb fragment of the KEX1-3' region that had been amplified using primers Kex 35 (CG GGATCCACTAGTATTTAAATCATATGTGCGAGTGTA CAACTCTTCCC ACATGG) (SEQ ID NO:36) and Kex 33 (GGACGCGTCGACGGCCTACCCGGCCGTACGAG GAATTTCTCGGATGAC TCTTTTC) (SEQ ID NO:37) with P. pastoris genomic DNA as a template was cloned into the cut plasmid to create pJN262. This plasmid was further cut with BamHI. The 3.8-kb BamHI, BglII fragment from pNKY51 (Alani et al., Genetics 116:541-545 (1987)) was then inserted into this site in both possible orientations to generate pJN263 and pJN264.

Figure 4:
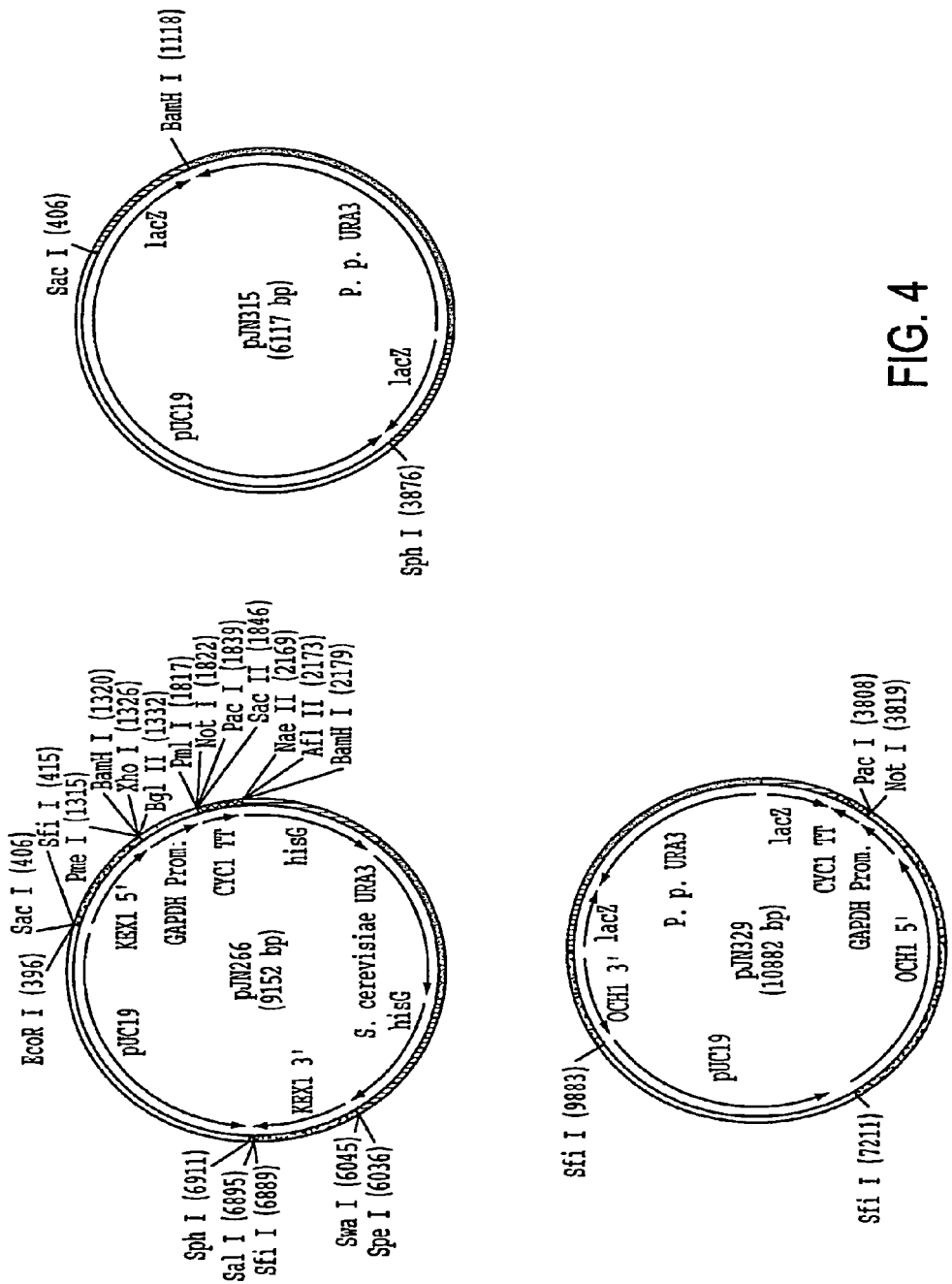
FIG. 4 shows restriction maps of plasmid pJN266 (including a recyclable URA3 cassette, which may be used to disrupt a KEX1 locus); plasmid pJN315 (including the *P. pastoris* URA3 gene flanked by lacZ direct repeats); and plasmid pJN329 (including a recyclable URA3 cassette, which may be used to disrupt an OCH1 locus).

An expression cassette was created using NotI and PacI as cloning sites. The GAPDH promoter of P. pastoris was amplified using primers Gap 5 (CG GGATCCCTCGAGAGATCTTTTTTGTAGAAATGTCTT GGTGCCT) (SEQ ID NO:38) and Gap 3 (GGACAT GCATGCACTAGTGCGGCCGCCACGTGATAGTTGTTC ATTGATTGAAATAGGGACAA) (SEQ ID NO:39) with the plasmid pGAPZ-A (Invitrogen, Carlsbad, Calif.) as a template. The amplified segment was cloned into the BamHI, SphI sites of pUC19 (New England Biolabs, Beverly, Mass.). The resulting plasmid was cut with SpeI and SphI. The CYC1 transcriptional terminator region was amplified using primers Cyc 5 (CCTTGCTAGCTTAATTAACCGCGGCACGTCC GACGGCGGCCCACGGGT CCCA) (SEQ ID NO:40) and Cyc 3 (GGACATGCATGCGGATCCCTTAAGAGCCGGC AGCTTGCAAATTAAAGC CTTCGAGCGTCCC) (SEQ ID NO:41) with plasmid pPICZ-A (Invitrogen, Carlsbad, Calif.) as a template. The amplified segment was cloned into the cut plasmid to create pJN261. The expression cassette was generated by digestion of this plasmid with BamHI. This fragment was cloned either into pJN263 (supra) to generate plasmid, pJN265, or into pJN264 (supra) to generate plasmids pJN266 and pJN267, depending on orientation of the insert. The map of pJN266 is shown in (FIG. 4).

A knockout plasmid for the P. pastoris OCH1 gene was created by digesting pJN263 with SalI and SpeI. A 2.9 kb DNA fragment of the OCH1-5' region, amplified using the primers Och55 (GAACCAC GTCGACGGCCATTGCGGCCAAAACCTTTTTTCCTA TTCAAA CACAAGGCATTGC) (SEQ ID NO:42) and Och 53 (CTCCAATACTAGTCGAAGATTATCTT CTACGGT-GCCTGGACTC) (SEQ ID NO:43) with P. pastoris genomic DNA as a template, was cloned into the open sites. The resulting plasmid was cut with EcoRI and PmeI. A 1.0-kb DNA fragment of the OCH1-3' region, amplified using the primers Och 35 (TGGAAGGTTTAAAC AAAGCTAGAG-TAAAATAGATATAGCGAGATTAG AGAATG) (SEQ ID NO:44) and Och 33 (AAGAATTCGGC TGGAAGGCCT-TGTACCTTGATGTAGTTCCCGTTTTCAT C) (SEQ ID NO:45) with P. pastoris genomic DNA as a template was inserted into the cut plasmid to generate pJN298. To allow for the possibility of simultaneously knocking out the OCH1 gene and introducing a new gene, the BamHI expression cassette of pJN261 (supra) was cloned into the unique BamHI site of pJN298 to create pJN299.

The P. pastoris gene disruption cassettes for URA3 and URA5 were constructed using a strategy similar to that described in Lu et al., Appl. Microbiol. Biotechnol. 49:141-146 (1998). A 2.0-kb PstI, SpeI fragment of the P. pastoris URA3 gene was inserted into the PstI, XbaI sites of pUC19 (New England Biolabs, Beverly, Mass.) to create pJN306. A 0.7-kb SacI, PvuII DNA fragment of the lacZ open reading frame from E. coli (see, e.g., Kalnins et al., EMBO J. 2:593-597 (1983)) was cloned into the SacI, SmaI sites to yield pJN308. Following digestion of pJN308 with PstI and treatment with T4 DNA polymerase, the SacI-PvuII fragment from lacZ, blunt-ended with T4 DNA polymerase, was inserted into the plasmid to generate pJN315 (FIG. 4). The lacZ/URA3 disruption cassette was released by digestion of pJN315 with SacI and SphI and blunt-ended with T4 DNA polymerase. The cassette fragment was then cloned into the backbone of pJN299 (supra) that had been digested with PmeI and AflII and blunt-ended with T4 DNA polymerase. The resulting plasmid was named pJN329 (FIG. 4). See also Choi et al., Proc. Natl. Acad. Sci. USA 100:5022-5027 (2003).

To generate a lacZ/URA5 disruption cassette, the SacI, PvuII fragment of lacZ was cloned into the SacI, SmaI sites of PUC19. The resulting plasmid was digested with PstI and blunted and the lacZ fragment that had been blunt-ended using T4 DNA polymerase was inserted into the plasmid to yield pJN316. A 1.0 kb fragment of the *P. pastoris* URA5 gene was amplified from the genomic DNA using primers Ura5Comp5 (GCTCTAGAGGGACTTATCTGGGTCCA GACGATGTG) (SEQ ID NO:46) and Ura5Comp3 (CG GGATCCGCCGCCGTGCCCAAAGCTCCGAAACAG) (SEQ ID NO:47) and cloned into the BamHI, XbaI sites of pJN316 to generate pJN396 (FIG. 5). The lacZ/URA5 cassette was released by digestion of this plasmid with EcoRI and SphI.

To create OCH1 knockout plasmids containing different auxotrophic markers, pJN299 (supra) was digested with PmeI and AflII and treated with T4 DNA polymerase. Following digestion of pJN315 (FIG. 4) with SacI and SphI, and digestion of pJN396 (FIG. 5) with EcoRI and SphI, each of the auxotrophic marker cassettes was blunt-ended with T4 DNA polymerase and ligated into the pJN299 backbone. This yielded plasmids pJN329 (URA3) and pJN398a (URA5), respectively.

Plasmid pJN398 was further modified by digestion with SpeI and NotI and blunt ended using T4 DNA polymerase. A blunt-ended BglII/HindIII fragment of pDL02 derived from Genbank Accession AF106080 (Abeijon et al., *Proc. Natl. Acad. Sci. USA* 93:5963-5968 (1996)) and containing the UDP-N-acetylglucosamine transporter of *K. lactis* was cloned into the open sites to create pJN407 (FIG. 5).

Example 4

Disruption of the *P. pastoris* OCH1 Gene and Regeneration of Counterselectable Markers The disruption of *P. pastoris* OCH1 in strain JC308 (ade1, arg4, his4, ura3) (Lin Cereghino et al., *Gene* 263:159-169 (2001)) using plasmid pJN329 (URA3) has been described in Choi et al. *Proc. Natl. Acad. Sci. USA,* 100:5022-5027 (2003), which is hereby incorporated by reference in its entirety.

To replace the *P. pastoris* OCH1 gene with the gene for the UDP-N-acetylglucosamine transporter of *K. lactis* using the URA5 counterselectable marker, 100 μg of pJN407 was digested with SfiI and transformed by electroporation into YJN165. Following incubation on minimal medium lacking uracil for ten days at room temperature, 460 colonies were picked and re-streaked. After three days, all 460 clones were streaked onto two sets of YPD plates. The five URA$^+$ clones that were unable to grow at 37° C., but that grew at room temperature, were subjected to colony PCR to test for the deletion of the *P. pastoris* OCH1 gene. All five strains gave rise to a PCR signal of the expected size. A second colony PCR confirmed that all five clones also contained the gene for the *K. lactis* UDP-N-Acetyl-Glucosamine Transporter. These clones were designated YJN198-1 through 5.

To regenerate the ura5 auxotroph, all five clones containing the och1::URA5 allele were grown on YPD plates for two days and then spread onto 5-FOA plates. After six days of incubation at room temperature, all five clones gave rise to colonies that were resistant to 5-FOA and that were also auxotrophic for uracil. The colonies resistant to 5-FOA that were derived by counterselection of YJN198-2 and YJN198-3 grew significantly slower than the others on YPD and were not examined further. The six fastest growing colonies that were derived by counterselection of YJN198-1, YJN198-4 and YJN198-5 were subjected to PCR analysis. These colonies were all confirmed to have lost the URA5 cassette. They were designated YJN199-1 through 6.

Figure 6:
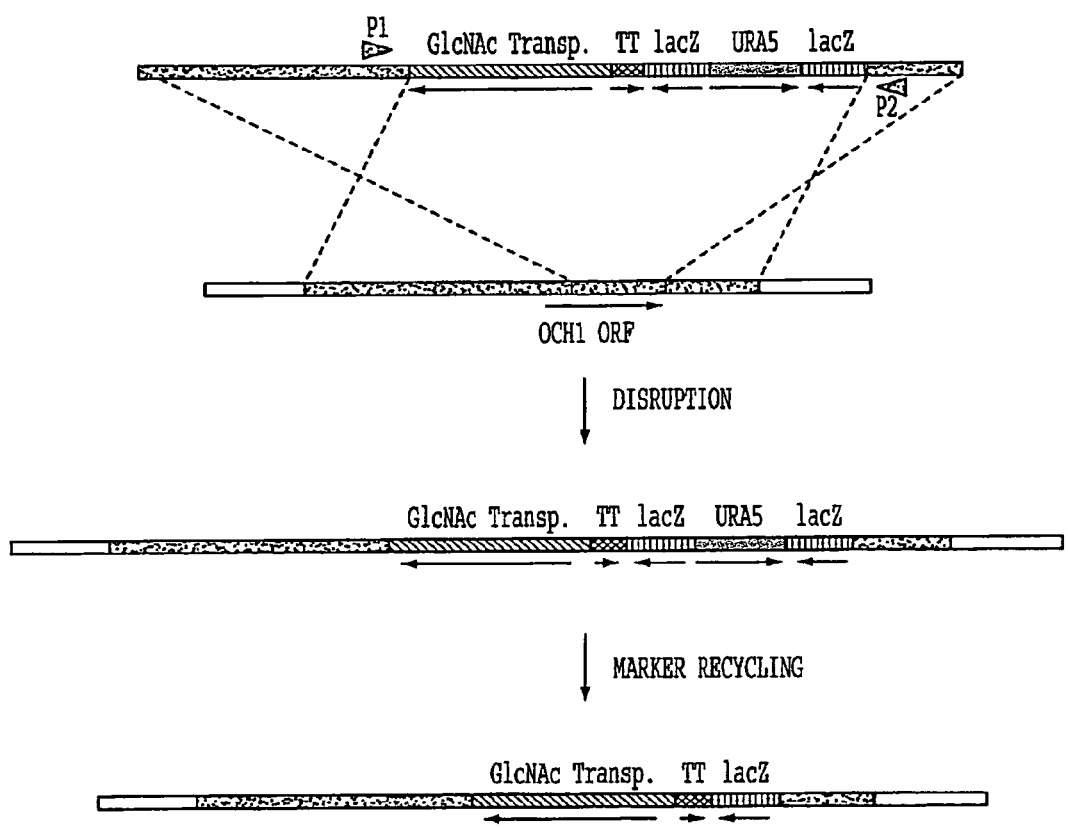
FIG. 6 shows the use of a *P. pastoris* URA5-*K. lactis* UDP-GlcNAc Transporter cassette in the stable integration of the UDP-GlcNAc Transporter into the OCH1 locus.

A schematic of the disruption and marker recycling steps occurring in the stable integration of the UDP-GlcNAc Transporter into the OCH1 locus using the *P. pastoris* URA5-*K. lactis* UDP-GlcNAc Transporter cassette is shown in FIG. 6.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

I claim:

1. An isolated polypeptide comprising or consisting of a polypeptide sequence selected from the group consisting of:
   (a) SEQ ID NO:3; and
   (b) a polypeptide sequence at least 95% identical to SEQ ID NO:3,
wherein the polypeptide has orotate-phosphoribosyl transferase activity.

2. A fusion protein comprising the isolated polypeptide of claim 1 fused to a heterologous amino acid sequence.

3. The fusion protein of claim 2, wherein the heterologous amino acid sequence is a detectable moiety.

* * * * *